(12) United States Patent
Tedesco et al.

(10) Patent No.: US 8,494,507 B1
(45) Date of Patent: Jul. 23, 2013

(54) ADAPTIVE, PORTABLE, MULTI-SENSORY AID FOR THE DISABLED

(75) Inventors: Daniel E. Tedesco, Shelton, CT (US); Robert C. Tedesco, Trumbull, CT (US); James A. Jorasch, New York, NY (US)

(73) Assignee: HandHold Adaptive, LLC, Shelton, CT (US)

( * ) Notice: Subject to any disclaimer, the term of this patent is extended or adjusted under 35 U.S.C. 154(b) by 0 days.

(21) Appl. No.: 13/540,148

(22) Filed: Jul. 2, 2012

Related U.S. Application Data

(62) Division of application No. 12/704,119, filed on Feb. 11, 2010, now abandoned.

(60) Provisional application No. 61/152,915, filed on Feb. 16, 2009.

(51) Int. Cl.
*H04M 3/00* (2006.01)
*G09B 21/00* (2006.01)
*G10L 11/00* (2006.01)
*G06F 3/00* (2006.01)

(52) U.S. Cl.
USPC ........... 455/418; 434/112; 704/271; 715/729; 715/865

(58) Field of Classification Search
USPC ................ 455/414.1, 418–420, 550.1, 552.1, 455/553.1, 556.1, 556.2, 557, 575.1–575.7, 455/463; 715/700–866; 345/418–475; 382/312–325; 434/111–117, 236–238; 704/271
See application file for complete search history.

(56) References Cited

U.S. PATENT DOCUMENTS

| | | | |
|---|---|---|---|
| 6,139,494 A | 10/2000 | Cairnes | |
| 6,542,623 B1* | 4/2003 | Kahn | 382/114 |
| 6,573,883 B1* | 6/2003 | Bartlett | 345/156 |
| 6,607,484 B2 | 8/2003 | Suzuki et al. | |
| 6,628,195 B1 | 9/2003 | Coudon | |
| 6,738,951 B1 | 5/2004 | Weiss et al. | |
| 6,944,474 B2* | 9/2005 | Rader et al. | 455/550.1 |
| 6,965,862 B2 | 11/2005 | Schuller | |
| 7,110,946 B2 | 9/2006 | Belenger et al. | |
| 7,251,605 B2 | 7/2007 | Belenger et al. | |
| 7,446,669 B2 | 11/2008 | Liebermann | |
| 7,741,962 B2 | 6/2010 | Kalik | |
| 7,766,828 B2 | 8/2010 | Ishii et al. | |
| 2005/0099291 A1 | 5/2005 | Landau | |
| 2005/0124375 A1* | 6/2005 | Nowosielski | 455/550.1 |
| 2006/0026001 A1* | 2/2006 | Bravin et al. | 704/270.1 |
| 2006/0129308 A1 | 6/2006 | Kates | |

(Continued)

OTHER PUBLICATIONS

Zhu, X. et al., "A text-to-picture synthesis system for augmenting communication," 6 pages, Apr. 2007, http://pages.cs.wisc.edu/jerryzhu/pub/ttp.pdf.

(Continued)

*Primary Examiner* — San Htun
(74) *Attorney, Agent, or Firm* — Withrow & Terranova, PLLC; Taylor M. Davenport

(57) ABSTRACT

A mobile terminal is used to assist individuals with disabilities. The mobile terminal (e.g., a "smartphone" or other commercially available wireless handheld device) may be loaded with software. The software may be configured to: (i) receive information about a sensory deficit associated with a user, (ii) receive information about a sensory proficiency associated with the user, (iii) determine whether an event associated with a sensory deficit satisfies a criterion, and if so (iv) provide an assistive output based on a sensory proficiency and the event.

17 Claims, 29 Drawing Sheets

U.S. PATENT DOCUMENTS

| | | | |
|---|---|---|---|
| 2006/0135139 A1* | 6/2006 | Cheng et al. | 455/418 |
| 2007/0218958 A1* | 9/2007 | Emery et al. | 455/569.1 |
| 2008/0318563 A1* | 12/2008 | Ross et al. | 455/418 |
| 2009/0174673 A1 | 7/2009 | Ciesla | |
| 2010/0041378 A1* | 2/2010 | Aceves et al. | 455/414.1 |

OTHER PUBLICATIONS

Adorni, G. et al., "Natural language driven image generation," 1984, 6 pages, http://www.aclweb.org/anthology/P/P84-1106.pdf.

Goldberg, A. et al., "Toward text-to-picture synthesis," 2009, 3 pages, http://www.davidriohardoon.com/AMD09/Schedule_files/ttp.pdf.

Phone Merchants, "Clarity amplified telephones and VCO telephones," 3 pages, Accessed Aug. 16, 2010, www.phonemerchants.com/clamteandvco.html.

Harris Communications, "Voice carry over TTY/HCO/Phone," 2 pages, Accessed Aug. 16, 2010, http://www.harriscomm.com/index.php/uti-1140.html.

ADCO Hearing Products, "What is TTY?, " 1 page, Accessed Aug. 16, 2010, http://www.adcohearing.com/tty_what_tty.com.

NC Hearing Loss, "Definition of VCO," 1 page, Accessed Aug. 16, 2010, http://nchearingloss.org/vco.htm?fromncshhh.

Phone Merchants, "Ameriphone hearing impaired visual smoke detector," 3 pages, Accessed Aug. 16, 2010, http://phonemerchants.com/amivissmokdet.html.

Phone Merchants, "Silent call shake-up with bed shaker," 5 pages, Accessed Aug. 16, 2010, www.phonemerchants.com/silcalshakwi.html.

Phone Merchants, "Guest room case 100," 3 pages, Accessed Aug. 16, 2010, http://www.phonemerchants.com/guroca100ein.html.

Phone Merchants, "Amplified speakerphone with big Braille buttons," 3 pages, Accessed Aug. 16, 2010, http://www.phonemerchants.com/amspwibigbrb.html.

Phone Merchants, "Talking programmable thermostat," 4 pages, Accessed Aug. 16, 2010, http://www.phonemerchants.com/tarpth.html.

Robotron Sensory Tools, "Galileo reading system," 3 pages, Accessed Aug. 16, 2010, http://www.sensorytools.com/galileo.htm.

Chandler, D., "MIT helps develop new image-recognition software," May 21, 2008, 3 pages, http://web.mit.edu/newsoffice/2008/csail-tt0251.html.

Engadget, "Mini microphone spruces up voice recording possibilities on iPhones/iPods," Feb. 24, 2009, 4 pages, http://www.engadget.com/2009/02/24/mini-microphone-spruces-up-voice-recording-possibilities-on-ipho/.

Engadget, "Video: 3D eye tracking from TAT, the guys behind the T-Mobile G1 UI," Feb. 24, 2009, 4 pages, http://www.engadget.com/2009/02/24/video-3d-eye-tracking-from-tat-the-guys-behind-the-t-mobile-g1/#continued.

Technology Review, "Cell phones that listen and learn," Jun. 22, 2009, 4 pages, http://www.technologyreview.com/communications/22907.

Salisbury, D., "Robots that monitor emotions of ASD children," Feb. 17, 2009, 12 pages, http://physorg.com/news/154119076.html.

Bio-Medical.com, 'GSR or galvanic skin response, 2 pages, Accessed Aug. 16, 2010, http://bio-medical.com/news_displays.cfm?mode=GSR&newsid=6.

NIH.GOV, "Continuous glucose monitoring," 5 pages, Accessed Aug. 16, 2010, http://diabetes.niddk.nih.gov/dm/pubs/glucosemonitor/index.htm.

Non-final Office Action for U.S. Appl. No. 12/704,119 mailed Feb. 2, 2012, 7 pages.

\* cited by examiner

Replacement Sheet

| RULE NO. | TRIGGER 1 | TRIGGER 1 TYPE | TRIGGER 1 SENSOR(S) | | DATE/TIME | OUTPUT TYPE(S) | OUTPUT CONTENT 1 | OUTPUT CONTENT 2 | OUTPUT CONTENT 3 |
|---|---|---|---|---|---|---|---|---|---|
| | | PROFILE NAME: JIMMY SMITH | | | PROFILE ID: P-0001 | | LOADED AS CURRENT PROFILE?: YES | | |
| 1 | DIRECT SUNLIGHT | LIGHTING | LIGHT SENSOR | o | ANY | VISUAL; AUDIO | "HI JIMMY, IS IT TOO..." | jimmyoutsid... | Sunglasses.GIF |
| 2 | 15 SECONDS OF ARM FLAPPING | PHYSICAL MOVEMENT | PERIPHERAL RING; MOTION SENSOR | o | ANY | AUDIO | Calmnote(1-26-... | HarvestMoon.MP3 | N/A |
| 3 | TRAMPOLINE | OBJECT NEAR MOBILE TERMINAL | OPTICAL CAMERAS | o | WED, 4:30 – 4:40 | VISUAL; AUDIO; TACTILE | TRAMPOLINE. MPEG | MED. VIBRATE; UNTIL PICKE DUP | N/A |

FIG. 28

| PROFILE ID: P-0001 | | | | | | | | |
|---|---|---|---|---|---|---|---|---|
| PROFILE NAME: JIMMY SMITH | | | LOADED AS CURRENT PROFILE?: YES | | | | | |
| SPD SURVEY QUESTION 1 | SPD SURVEY QUESTION 2 | SPD SURVEY QUESTION 3 | OLFACTORY IMPAIRMENT | HYPERACUSIS | TINNITUS | TINNITUS TYPE | TINNITUS SEVERITY | |
| ALWAYS | FREQUENTLY | NEVER | YES | NO | YES | PULSATILE | MODERATE | |
| VISUAL ACUITY | TACTILE AVOIDANCE 1 | TACTILE AVOIDANCE 1 SEVERITY | LEFT EAR @ 250 Hz | RIGHT EAR @ 250 Hz | LEFT EAR @ 500 Hz | RIGHT EAR @ 500 Hz | LEFT EAR @ 1000 Hz | |
| 20/30 | SAND | SEVERE | 20 dB | 15 dB | 20 dB | 20 dB | 20 dB | |

FIG. 29

ADAPTIVE, PORTABLE, MULTI-SENSORY AID FOR THE DISABLED

RELATED APPLICATIONS

The present application is a divisional application of U.S. patent application Ser. No. 12/704,119, filed Feb. 11, 2010, now abandoned.

The '119 application claimed the benefit of and priority to U.S. Provisional Patent Application Ser. No. 61/152,915 filed Feb. 16, 2009.

The contents of the applications listed above are hereby incorporated by reference in their entireties.

FIELD OF THE INVENTION

The present application is directed to assisting those with sensory deficits through the use of a mobile terminal.

BACKGROUND

With a growing population, the number of developmentally disabled children grows. Additionally, the rates at which children have been diagnosed as developmentally disabled, and particularly diagnosed with autism spectrum disorders (ASD), have steadily increased. Individuals with developmental disabilities often have several challenges in common, including but not limited to speech and language impairments, cognitive deficits, social problems, behavioral problems, memory problems, attention deficits, and sensory processing dysfunction. The developmentally disabled population extends beyond those with ASD to include those with Down syndrome, cerebral palsy, Fragile X syndrome, and other disabilities which may involve sensory impairments. In addition, many individuals develop sensory deficits at later stages in life, from trauma, old age, or other neuropathy. More than eight million people over the age of five in the United States alone are hard of hearing. More than seven million are visually impaired. Sensory dysfunction can result from stroke, brain injury, cancer, and other ailments.

For individuals with sensory processing dysfunction any number of conditions such as: hypersensitivity or hyposensitivity with respect to senses of sight; hearing; touch; smell; taste; pain (nociception); balance (equilibrioception), spatial orientation, joint motion and acceleration (proprioception and kinesthesia); time; and temperature (thermoception) may pose significant challenges in simple daily tasks, particularly when such tasks involve new environments. Many take for granted the ability to visit a new place, walk in sunlight, cope with the general auditory din of a public location, interact with a pet, and so on, though these tasks may be particularly daunting for hypersensitive individuals. For the hyposensitive, difficulty hearing, feeling, seeing, or balancing presents a constant battle, forcing many to overcompensate for their deficits (e.g., aggressively bang an object simply to feel it), or exhaust themselves straining a particular sense. Many disabled individuals resort to self-stimulatory or "stereotypy" activity (e.g., echolalic or perseverative speech, repetitive body motions, etc.) as a mechanism to cope with or regulate sensory irregularities.

BRIEF DESCRIPTION OF THE DRAWINGS

FIG. 28 illustrates a first example database suitable for use with the present disclosure.

FIG. 29 illustrates a second example database suitable for use with the present disclosure.

DETAILED DESCRIPTION

Described herein are techniques for assisting individuals with disabilities. In some embodiments, a mobile terminal (e.g., a "smartphone" or other commercially available wireless handheld device described herein) may be loaded with software of the present disclosure. The software may be configured to: (i) receive information about a sensory deficit associated with a user, (ii) receive information about a sensory proficiency associated with the user, (iii) determine whether an event associated with a sensory deficit satisfies a criterion in that an event has occurred that relates to or implicates the sensory deficit, and if so (iv) provide an assistive output based on a sensory proficiency and the event. In one embodiment, a sensory input is received by the software and translated into a sensory output that is more easily understood or processed by a user of a mobile terminal. For example, a user with auditory hypersensitivity may receive information about a loud environment (the presence of the loud environment implicates the auditory hypersensitivity) by way of a text shown on a display screen. In another example, a user with visual hypersensitivity may receive information about an overly bright environment through audio speakers or a peripheral headset. As an alternative to (or in addition to) such sensory translations, the software may provide therapeutic or instructional output to help the disabled individual cope with the event (e.g., soothing music, a vibration, advice for how to cope with the situation, a reassurance that a caregiver is nearby, or the like).

Figure 1:
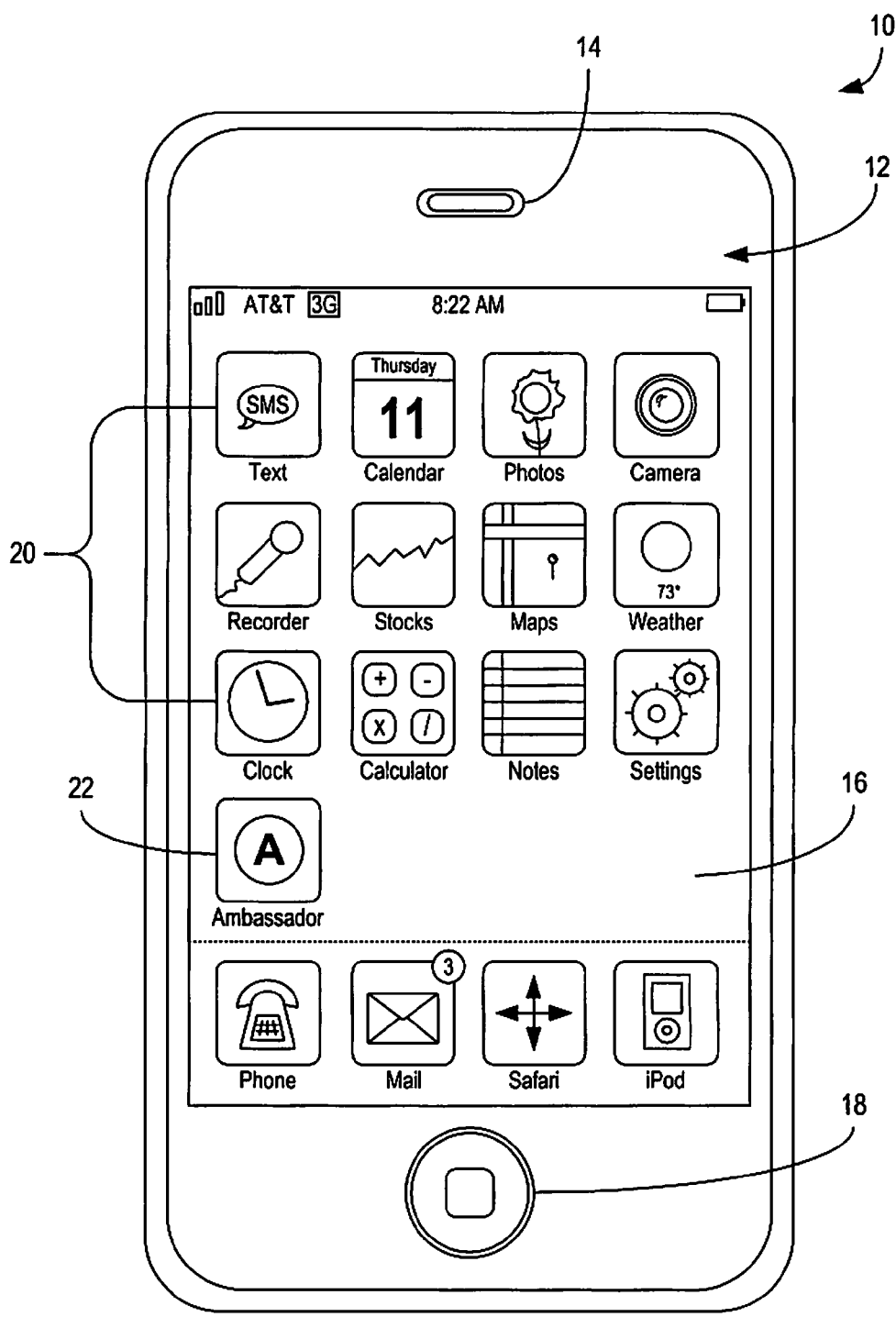
FIG. 1 illustrates a front elevational view of a mobile terminal.

An overview of some of the hardware elements is provided before addressing some of the methods and potential screen configurations associated with embodiments of the present disclosure. A mobile terminal 10 is illustrated in FIG. 1. An exemplary suitable mobile terminal 10 may be the APPLE® IPHONE™ (or IPOD™) and may include a user interface 12 that includes a speaker 14, a microphone 26 (FIG. 2), a touch screen display 16, and a command entry button 18. One or more icons 20 may be displayed on the touch screen display 16. The user may enter commands by touching an icon or element on the touch screen display 16 or by using the command entry button 18 as is well understood. One such icon 22 may launch software that effectuates embodiments of the present disclosure. While the IPHONE™ is particularly contemplated, the disclosure is not so limited, and any readily portable handheld computing device may be appropriate including personal digital assistants, cellular telephones, (e.g., so called "smartphones"), WINDOWS MOBILE™ enabled devices, or the like. Further examples of such mobile terminals include, but are not limited to: the BLACKBERRY™ line of wireless devices manufactured by Research in Motion of Waterloo, Ontario, Calif.; the T-MOBILE G1™ or other mobile terminals compatible with the ANDROID operating system as developed by Google, Inc. of Mountain View, Calif.; the PRADA™ or other mobile terminals manufactured by LG ELECTRONICS MOBILECOMM U.S.A, INC. of San Diego, Calif.; the INSTINCT™ or other mobile terminals manufactured by SAMSUNG TELECOMMUNICATIONS AMERICA, LLC; the XPERIA™ X1 or other mobile terminals manufactured by SONY ERICSSON MOBILE COMMUNICATIONS AB of Sweden; the N96 or other mobile terminals manufactured by NOKIA GROUP of Finland; and the PRE™ or other mobile terminals manufactured by PALM, INC. of Sunnyvale, Calif. In other embodiments, a mobile terminal may comprise a portable personal computer with a sufficiently large, touch-sensitive screen (e.g., a "tablet" or "tablet computer" such as the APPLE® IPAD™).

Figure 2:
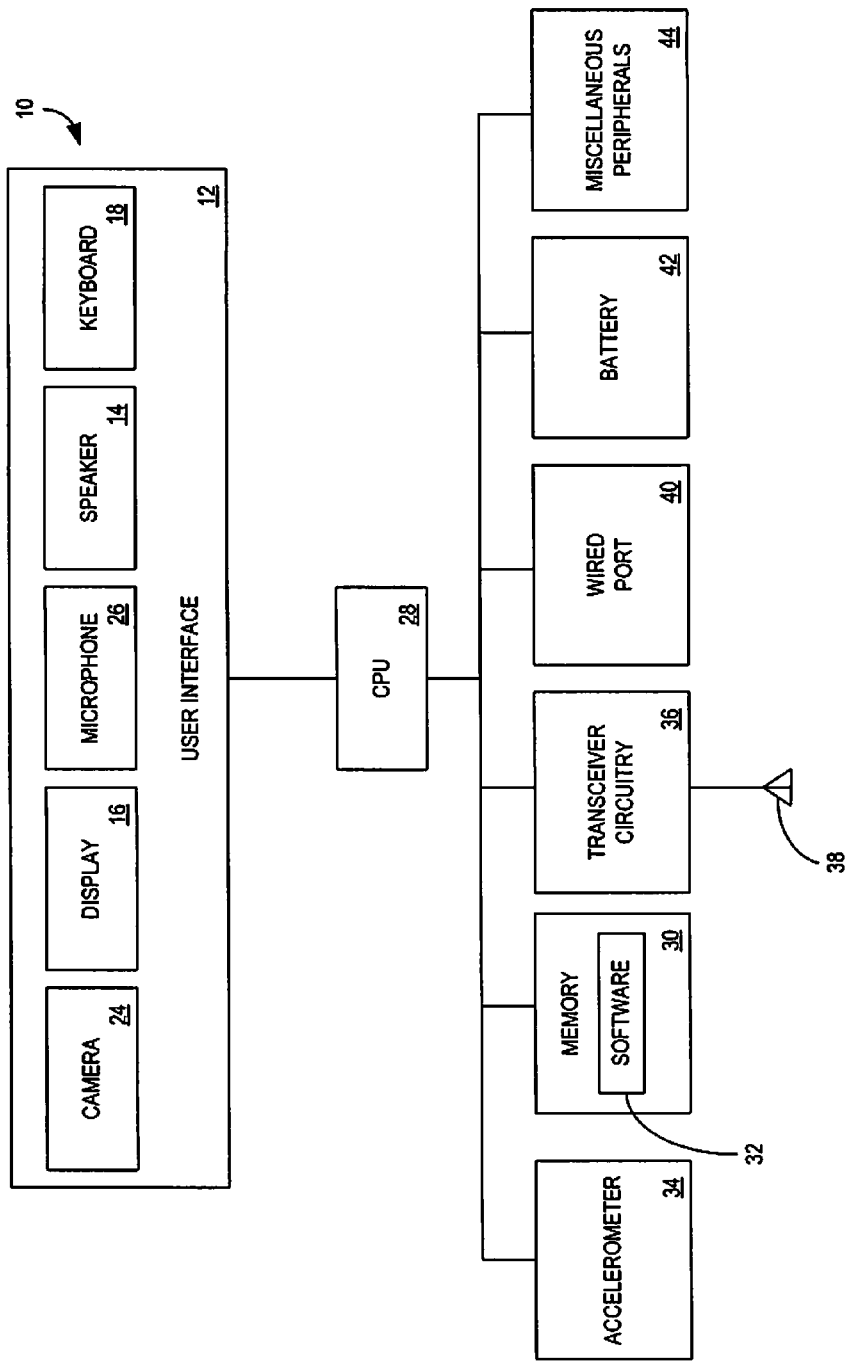
FIG. 2 illustrates a block diagram of the components of a conventional mobile terminal.

A block diagram of the mobile terminal 10 is illustrated in FIG. 2. The mobile terminal 10 includes the elements already illustrated and further includes, within the user interface 12, a camera 24 and the aforementioned microphone 26. The user interface 12 is operatively coupled to a central processor (CPU) 28. The CPU 28 is also operatively coupled to memory 30 with software 32 stored therein, an accelerometer 34, transceiver circuitry 36, which in turn is coupled to an antenna 38, one or more wired ports 40, a battery 42, and any other miscellaneous peripherals 44 as is common in the mobile terminal art (e.g., an internal clock, a vibration unit, a Global Positioning System (GPS) receiver, a thermometer, a light sensor, a proximity sensor, an altimeter, a pressure sensor or the like). To the extent that such elements may interact with the user, they may also be considered part of the user interface even if not explicitly labeled such. For example, when a vibration unit vibrates, the user interacts with it by feeling the vibration. Likewise, the output of the GPS receiver may be perceived by the user through the display 16, through an output of the speaker 14, or the like. Any such miscellaneous peripherals 44 may alternately or additionally be embodied as separate peripheral devices in communication with mobile terminal 10 (rather than as a component thereof). The CPU 28 as operated under the instructions of the software is a control system as that term is defined in the Rules of Interpretation & General Definitions set forth below. It should be understood that the hardware configuration depicted by FIG. 2 is illustrative and that mobile terminal 10 may comprise other types of hardware, either as components of the mobile terminal 10, or as peripheral devices in communication with the mobile terminal 10. Such separate peripheral devices are discussed further below with respect to FIG. 4.

Figure 3:
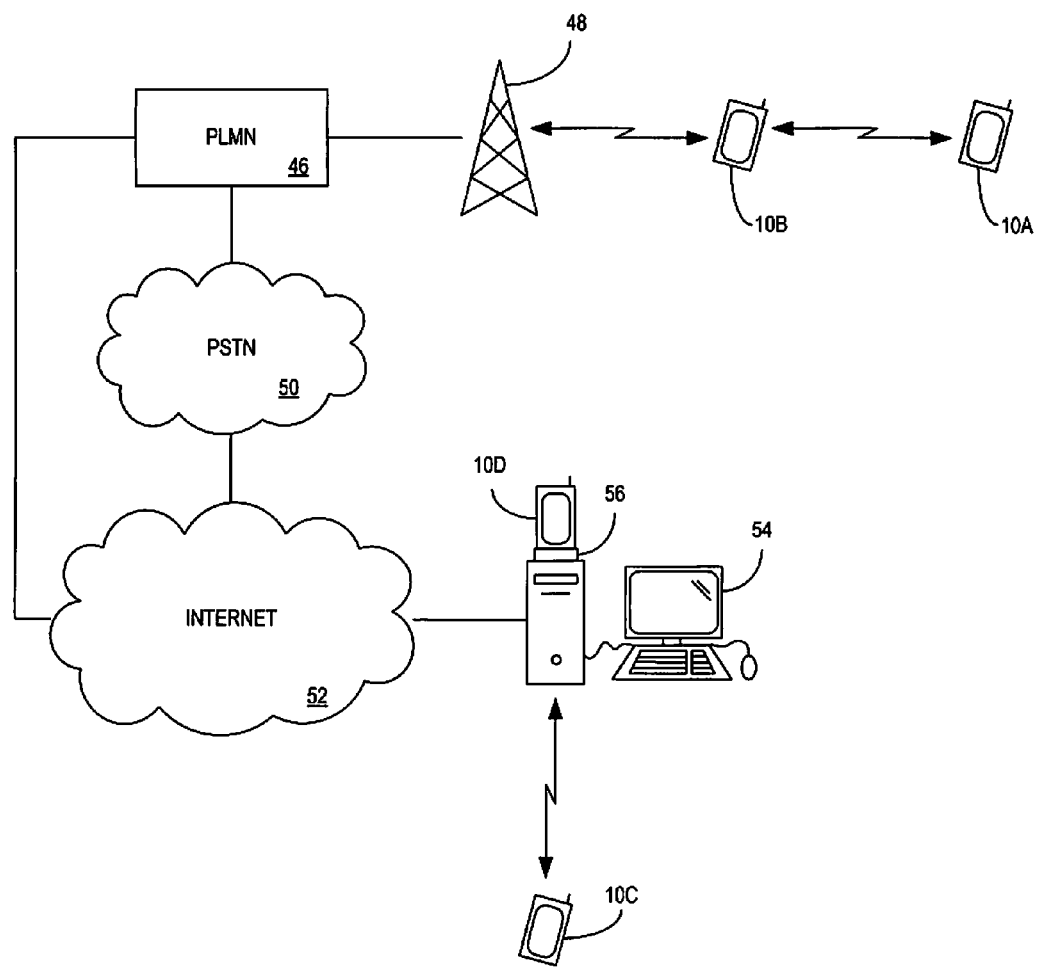
FIG. 3 illustrates a variety of networks in which a mobile terminal may operate.

FIG. 3 illustrates a variety of networks through which mobile terminals 10 may communicate. For example, a first mobile terminal 10A may communicate with a second mobile terminal 10B through a local wireless network/protocol such as a BLUETOOTH™, infrared, or other short range communication protocol. Additionally, or alternatively, the second mobile terminal 10B may communicate with a cellular network such as the Public Land Mobile Network (PLMN) 46 through a cellular base station 48. The PLMN 46 may communicate with the Public Switched Telephone Network (PSTN) 50 and/or the Internet 52. One or more computers 54 may be communicatively coupled to the Internet 52 and may include a wireless transceiver to communicate wirelessly with a third mobile terminal 10C or a docking station to communicate via a wired line with a fourth mobile terminal 10D. More information on networks and communication protocols can be found in the Rules of Interpretation and General Definitions set forth below. Suffice to say that the particular network or communication protocol is not central to embodiments of the present disclosure. Additionally, it should be understood that such protocols may enable communications between mobile terminals and various peripheral devices, including sensors, cameras, microphones, and the like.

Figure 4:
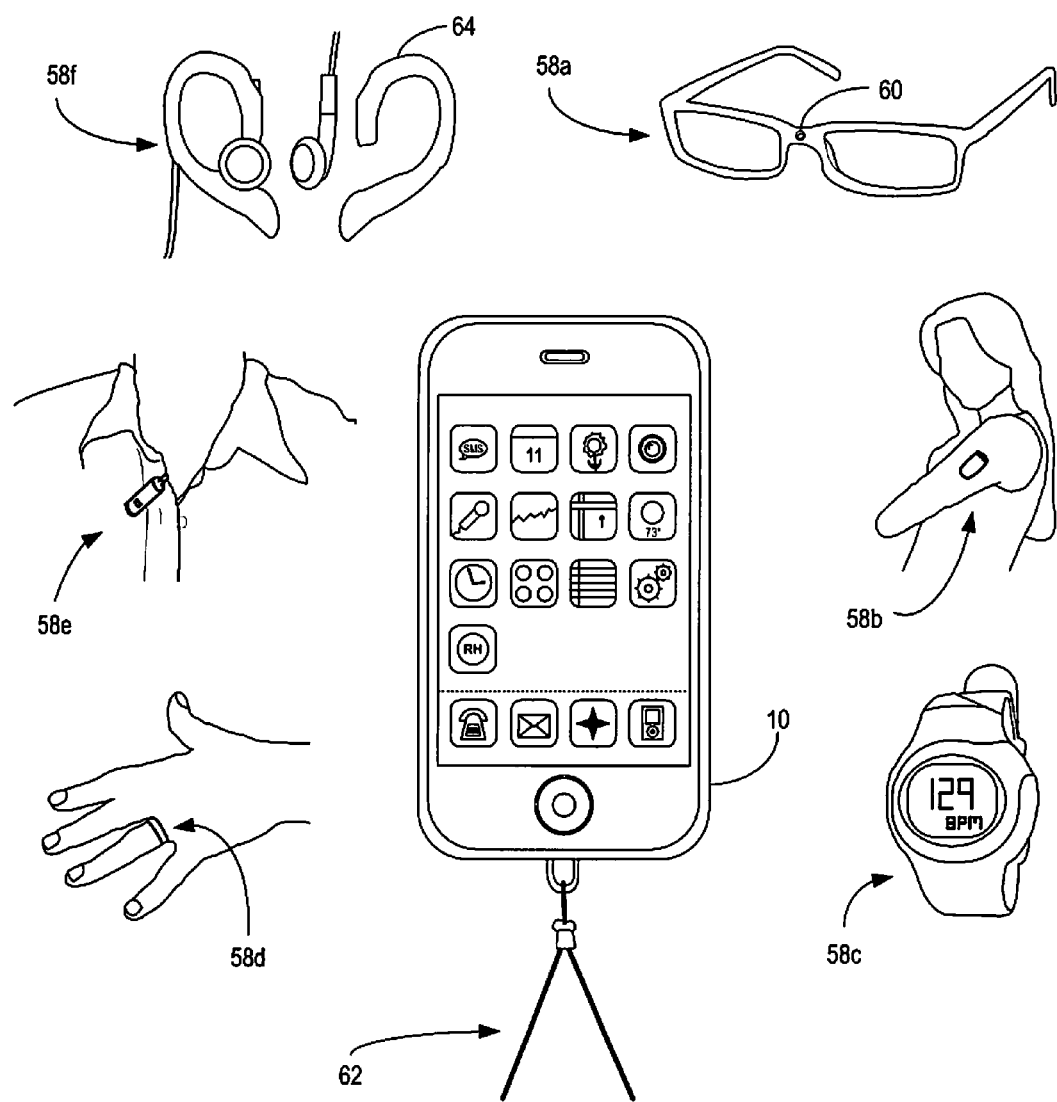
FIG. 4 illustrates various devices which may interface with a mobile terminal.

FIG. 4 illustrates an assortment of such peripheral devices 58a-f. While other devices may communicate with the mobile terminal 10 as described in this disclosure, a few are specifically shown. An application programming interface (API) may enable interaction between software of the present disclosure and such separate devices. Communication methods which may be utilized between the peripheral devices and the mobile terminal 10 include wireless protocols referenced above (e.g., BLUETOOTH™, infrared), radio frequency identification (RFID), WiFi, and hard wiring.

Peripheral eyeglasses 58a may communicate with the mobile terminal 10, and may comprise an optical camera 60, a RFID transponder (not shown), an audio microphone (not shown), accelerometer (not shown), and/or an infrared transmitter (not shown). Eyeglasses 58a may be used to provide information related to (i) the environment surrounding an individual wearing the eyeglasses (e.g., still images or video are taken from outward-facing optical camera 60 and transmitted to mobile terminal 10 through eyeglasses 58a), (ii) pupil dilation of the individual wearing the glasses (e.g., optical-camera 60 is oriented inward to directly monitor the user's eyes), or (iii) the direction of the individual's gaze with respect to the mobile terminal (e.g., the orientation of eyeglasses 58a relative to mobile terminal 10 is determined using RFID, and thus the orientation of the individual's gaze relative to mobile terminal 10 may be inferred). As an example of eye-tracking technology used in conjunction with a mobile terminal, the 3D Eyetracking UI as developed by TAT THE ASTONISHING TRIBE, AB of Sweden for the T-MOBILE G1 mobile terminal alters the user-interface presented by the mobile terminal's display screen based on the orientation of the device to the user's eyes.

Peripheral skin patch 58b may comprise (i) a sensor enabling the measurement of biological properties, and (ii) a transmitter enabling wireless communication with mobile terminal 10. Biological properties measured by skin patch 58b may include temperature, blood glucose (the GUARDIAN® REAL-Time Continuous Glucose Monitoring System, as produced by MEDTRONIC MINIMED, INC. of Northridge, Calif., comprises a sensor embedded within a skin patch that monitors blood sugar levels and a transmitter to send data wirelessly to a receiver via BLUETOOTH™), blood pressure, Galvanic Skin Response (GSR) or electrodermal skin response, heart rate, and cardiac electrical activity (e.g., a wireless ECG patch such as the one developed by the IMEC research center in Belgium). Thus, a user of mobile terminal 10 may also wear skin patch 58b such that biological measurements may be taken in a continuous, periodic, or otherwise specified manner.

Wristwatch 58c may measure and transmit biological data in a manner similar to that of skin patch 58b. Thus, a user of mobile terminal 10 who enjoys wearing a watch may at the same time provide a variety of biological data used by the software of the present disclosure. A variety of commercially available digital wristwatches comprise sensors for measuring such data (e.g., the IRONMAN® Heart Rate Monitor Watch by TIMEX®). In an alternate embodiment, wristwatch 58c may instead take the form of a basic wristband, arm band or ankle band (i.e., comprising a sensor and transmitter but no clock or stopwatch functionality). Likewise, while not shown, the wristwatch 58c may also include an accelerometer, an RFID transponder, or the like to detect movement of the wristwatch 58c or its position relative to the mobile terminal 10.

Ring 58d may also measure and transmit biological data and/or positional data in a manner similar to that of skin patch 58b. The ring 58d and its components (e.g., sensors, electronics) may be fashioned from a variety of metals, plastics, composites, and/or semiconductors. In one embodiment, a commercially available ring, such as the MYBEAT Heart Rate Ring by LIFESPAN FITNESS, may be adapted for use with software of the present disclosure.

In one embodiment (not shown), a biosensor may be permanently affixed to or implanted beneath the user's skin. For example, a subcutaneous electrochemical sensor may be used to continuously measure and report on blood (or interstitial fluid) glucose level. An example of a device employing such a semi-permanent sensor is the FREESTYLE NAVIGATOR® Continuous Glucose Monitoring System by ABBOTT LABORATORIES of Abbott Park, Ill.

Clip-on microphone 58e may be used to receive audio data and re-transmit it to the mobile terminal 10. Thus, if the clip-on microphone 58e is oriented toward the user's mouth (as it appears in FIG. 4), the user of mobile terminal 10 may act and speak naturally, with the user's speech transmitted automatically to mobile terminal 10. In another embodiment, the clip-on microphone 58e may be oriented away from the user such that sounds occurring in front of the user may be captured (e.g., fastened to a lapel as in FIG. 4, but facing outward; fastened to a belt clip, purse, or other area; etc.). In one embodiment (not shown), a microphone and speaker may both exist as part of a wireless headset worn by a user of mobile terminal 10 (e.g., affixed via an ergonomic piece of plastic so as to rest around a user's ear). Suffice it to say that wireless microphones of a variety of sorts are widely available in the commercial marketplace, well known in the mobile terminal art, and may be used in conjunction with software of the present invention.

Headphones 58f may be employed as a mechanism to hear audio produced by mobile terminal 10 (e.g., as an alternate to, or in addition to, speaker 14). In one embodiment, headphones may take the form of earbuds, and along with ergonomic plastic 64, may be positioned in a manner that is secure, comfortable, and effective for listening to sounds produce by the mobile terminal 10. In other embodiments, a full set of ear-encompassing headphones may be used. As alluded to above, headphones 58f may also be incorporated into a single device with a microphone 58e (not shown). Suffice it to say that headphones of a variety of sorts are widely available in the commercial marketplace and may be used in conjunction with software of the present invention. In some embodiments, such headphones may incorporate other sensors (e.g., RFID, an infrared sensor, a motion sensor) to facilitate embodiments of the present disclosure (e.g., determination of the physical orientation of the user's head).

Worth discussing at this point is the manner in which mobile terminal 10 may be carried or held. In various embodiments, a mobile terminal 10 may be carried or held by a disabled individual and/or a physically present caregiver. At times, mobile terminal 10 may be carried by hand, but this may not always be desirable, convenient, or possible. While the above described peripheral devices 58 may allow for the placement of mobile terminal 10 inside of a pocket or a purse, some embodiments (e.g., those requiring substantially continuous use of components integrated within mobile terminal 10 itself) may benefit from the placement of mobile terminal 10 outside of a pocket or a purse. In one embodiment, as depicted in FIG. 4, a lanyard 62 may be attached to mobile terminal 10 (or, attached to an after-market case designed to protect the mobile terminal 10 from wear and tear), such that mobile terminal 10 may hang from the neck of an individual, rather than be held by hand, within a pocket or within in a purse. Other cases (not shown) that fasten mobile terminal 10 to the body or clothing may be used, including arm bands, wrist bands, belt clips, and the like. Still further cases (also not shown) may affix mobile terminal 10 to wheelchair arms, head pointers, or other physical devices used to afford the disabled with mobility or the ability to communicate. Peripheral devices 58 may be similarly affixed to such locations or objects.

In some embodiments, a user of the mobile terminal 10 may be reminded or encouraged to appropriately position the mobile terminal 10 or any associated peripheral devices on or around his or her person. For example, in some embodiments, placement of the mobile terminal 10 around the neck of a disabled user through the use of lanyard 62 may be desirable. Thus, if the mobile terminal's integrated light sensor detects lack of light for a prolonged period of time during a specified coverage period (e.g., suggesting that the device may be in the user's pocket or purse), a vibration unit, speaker 14, or other output device may be actuated to alert the user and encourage him or her to appropriately position the mobile terminal 10 (e.g., the mobile terminal vibrates, and the speaker outputs a ringtone or other alarm). An accelerometer 34 and/or light sensor may then detect that the device has been picked up, at which point instructions for effectively positioning the device may be output (e.g., the display screen 16 outputs a graphical indication of the device hung around a neck, while speaker 14 outputs an audio instruction to "Hang around your neck, please!"). Placement of the mobile terminal 10 or associated peripheral devices in other locations may be encouraged in a similar manner (e.g., a user is encouraged to position peripheral microphone 58e outward such that it captures the speech of those engaged in conversation with the user).

Figure 5:
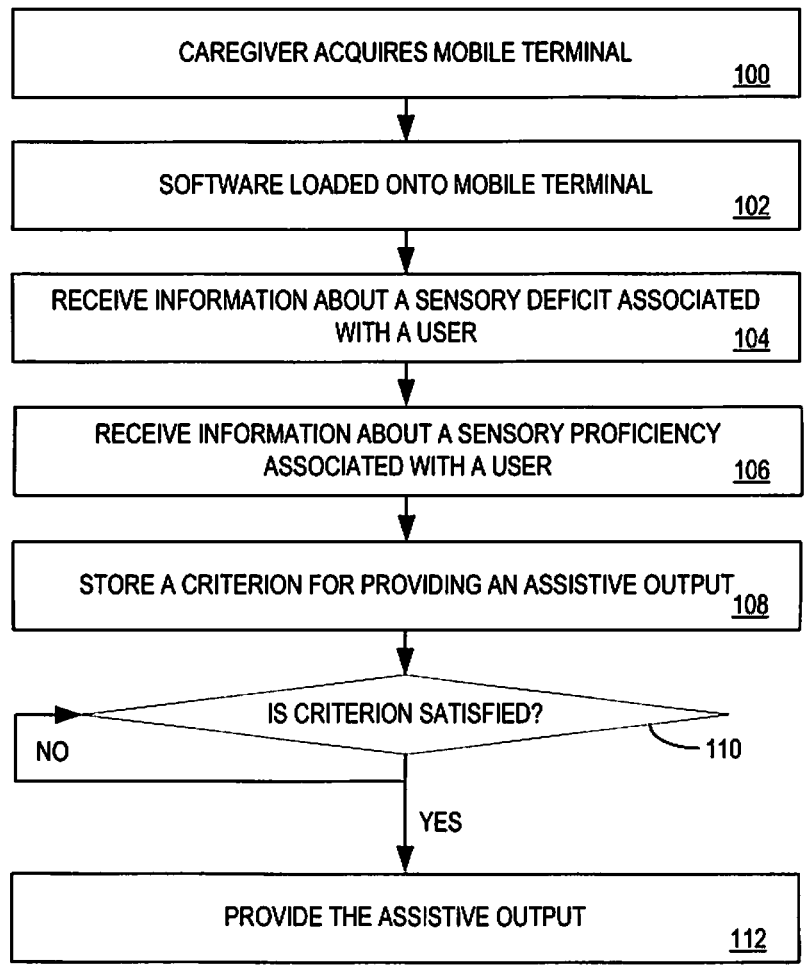
FIG. 5 illustrates a first flow chart showing an exemplary embodiment of the present disclosure.

Against this backdrop of hardware, an overview of an exemplary method is presented starting with reference to FIG. 5 as a flow diagram interspersed with additional Figures for supporting explanatory and exemplary screen shots. Initially, a user acquires a mobile terminal 10 (block 100). This acquisition may be a gift, a purchase, a lease, borrowing, or otherwise. For example, the disabled individual may purchase the mobile terminal 10 and loan it to the caregiver for the purposes of carrying out embodiments of the present disclosure. Alternatively, the caregiver may purchase the mobile terminal 10 for use by and/or with the disabled individual. The caregiver may load the software embodying the present disclosure onto the mobile terminal 10 (block 102). If the mobile terminal 10 has a disk drive or other data storage device or functionality (e.g. flash memory), the software may be loaded from a disk or other source. Otherwise, the software may be loaded onto a computer 54 (e.g., via disk transfer or download) and transferred to the mobile terminal 10 through the docking station or wirelessly. As still another alternative, the mobile terminal 10 may download the software through the PLMN 46 or other technique as desired. The software could be preloaded on the mobile terminal 10 such that when the lease or purchase is made, the software is immediately accessible. The software itself may be free, paid or subsidized in whole or part by a third party (such as a school district or other governmental agency or private foundation). Note that while it is contemplated that the caregiver performs these and other steps, it is also possible that the disabled individual performs these and the other steps.

The caregiver may then configure elements of the software, so as to customize the software on behalf of a disabled individual. Particularly, the caregiver may provide the software with information about one or more sensory deficits associated with a user, and thus the software receives information about a sensory deficit associated with the user (block 104). For example, one or more particular hypersensitivities or hyposensitivities associated with a disabled user may be described. The software may further receive information about a sensory proficiency associated with the user (block 106). Further, the caregiver may provide, and the software may store, a criterion for providing an assistive output as well as the actual assistive output (block 108). The provided information is saved, and the software, through the sensors associated with the mobile terminal 10 monitors the activities of the disabled individual to determine if the criterion has been satisfied (block 110). If the criterion has been satisfied, the mobile terminal 10, or an associated peripheral device 44 or 58 may be used to provide an assistive output. Many of these steps will be further explained below with reference to various exemplary screen shots.

In an exemplary embodiment, after the software is loaded onto the mobile terminal (block 104, FIG. 5), the caregiver accesses the software, such as by pressing the icon 22. Once the software has launched, the caregiver may be presented with a screenshot such as that illustrated in FIG. 6 (or one with comparable functionality). From this screen, the caregiver may configure the software as further described below. Alternatively, the caregiver may configure the software through another mechanism such as by selecting a "Settings" icon from a group of icons 20 displayed by the mobile terminal 10. As yet another alternative, computer 54 may be used to configure software settings, which may then be transmitted to a mobile terminal 10 using methodologies described above (e.g., a caregiver uses Web-based software on a personal computer to provide sensory deficit information, such that the information is saved to a central database and subsequently accessible wirelessly by the mobile terminal 10; a caregiver uses a software program of a personal computer to provide sensory deficit information, and the information is subsequently transferred from computer 54 to mobile terminal 10 via docking station).

Figure 6:
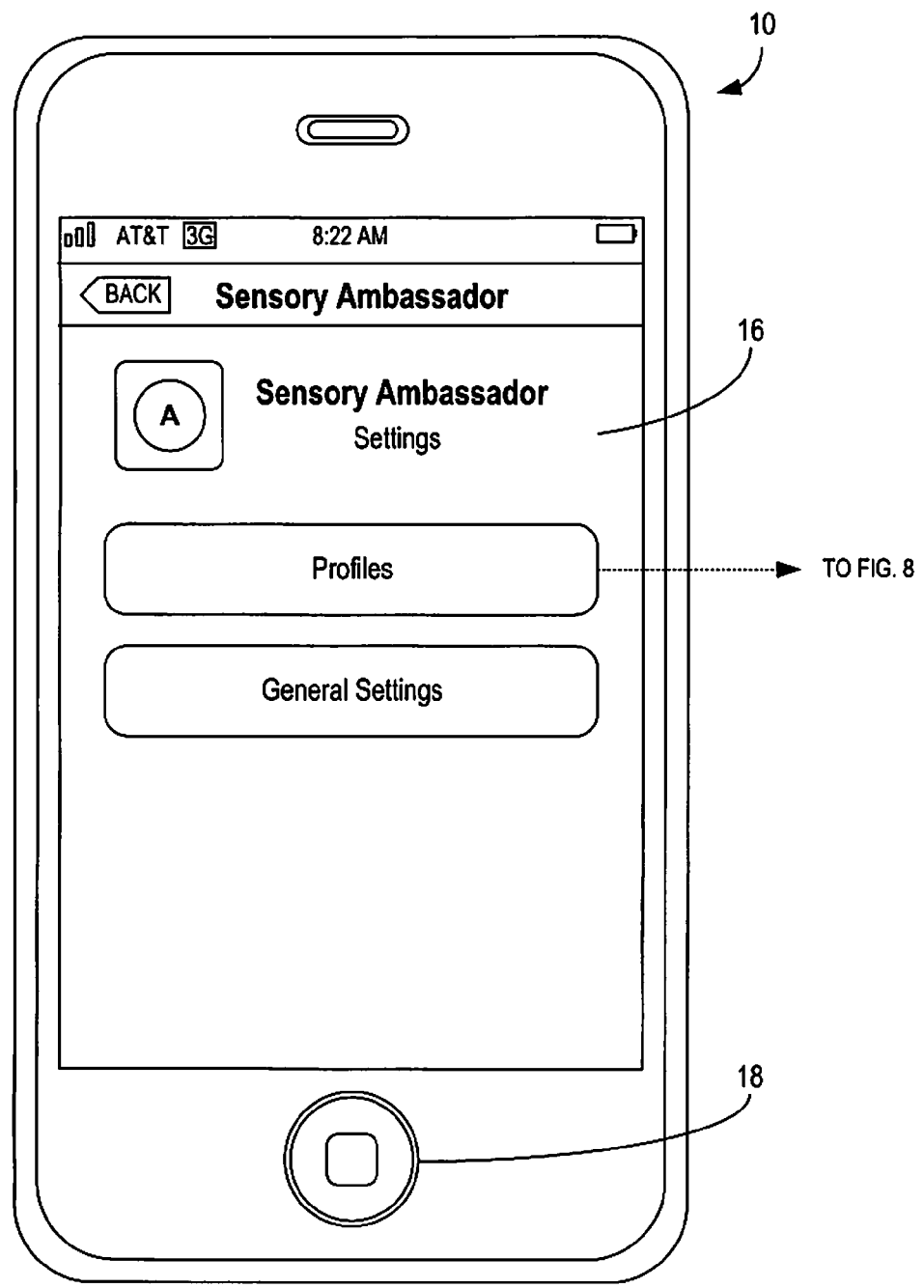
FIG. 6 illustrates a first screen shot associated with the flow chart of FIG. 5.
Figure 7:
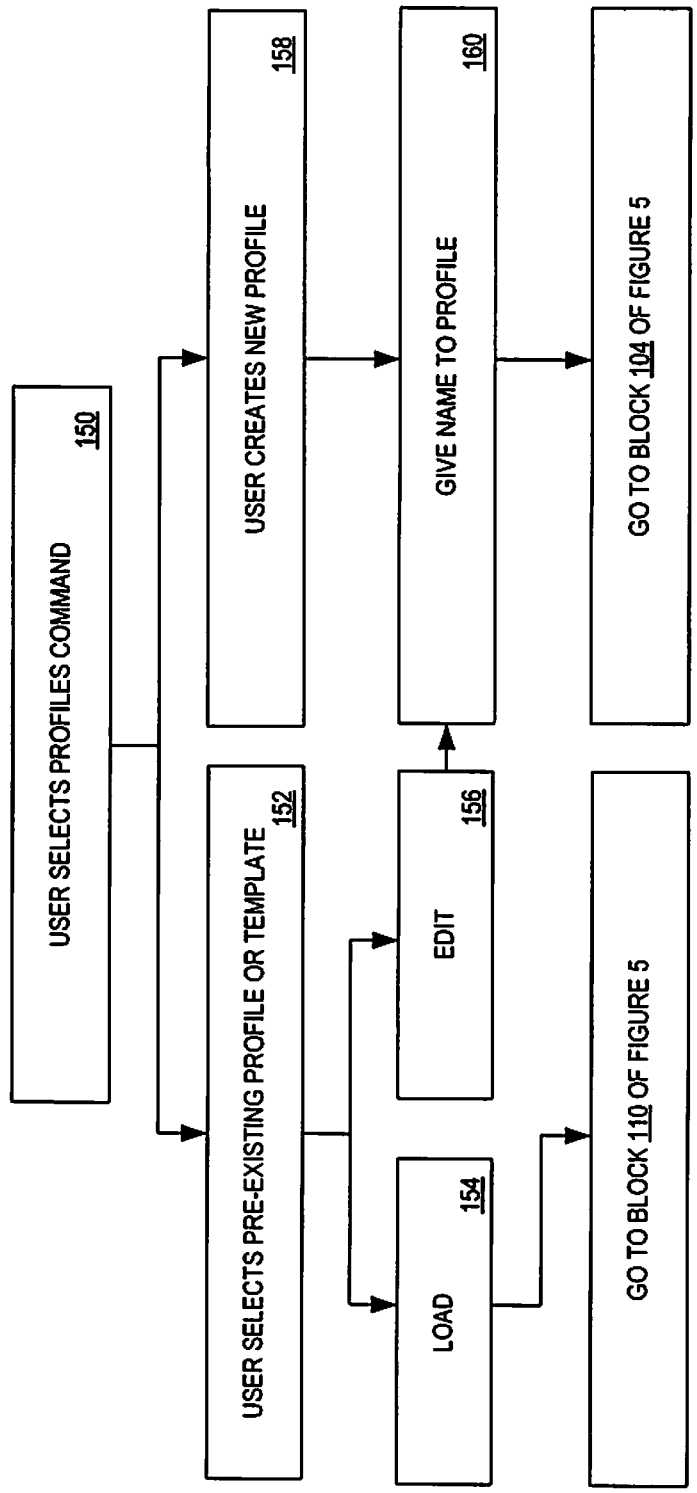
FIG. 7 illustrates a second flow chart further explaining a sub-process within the process of FIG. 5.
Figure 8:
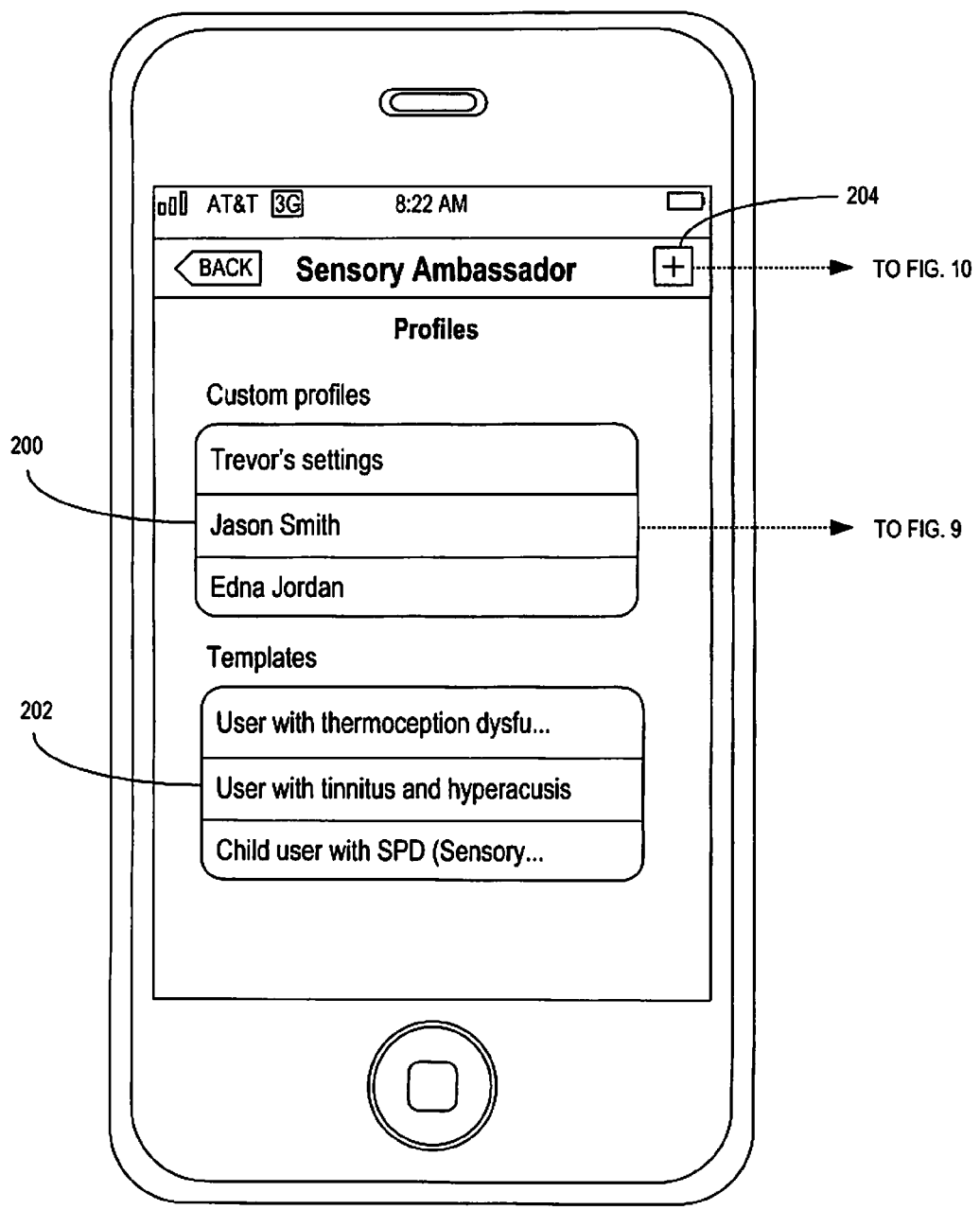
FIG. 8 illustrates a second screen shot associated with the flow chart of FIG. 5.

Regardless of the particular technique, the caregiver may see a screen such as that illustrated in FIG. 6. Specifically, as shown, the caregiver may be presented with a "Profiles" command and a "General Settings" command. In block 150 of FIG. 7, the user selects "Profiles", in which case the user may see a screen such as that shown in FIG. 8 (or screen with comparable functionality), where the user may select from profiles 200 that the user has previously created or from default pre-existing templates 202, or create a new template by activating the "+" command 204 (e.g., add new profile) in the upper corner. The "General Settings" may allow the user to configure certain default parameters that are not implicated by other rules within the software (e.g., if the user has auditory neutral, a default volume may be set; if the user is visual neutral, a default brightness may be set; or the like).

Figure 9:
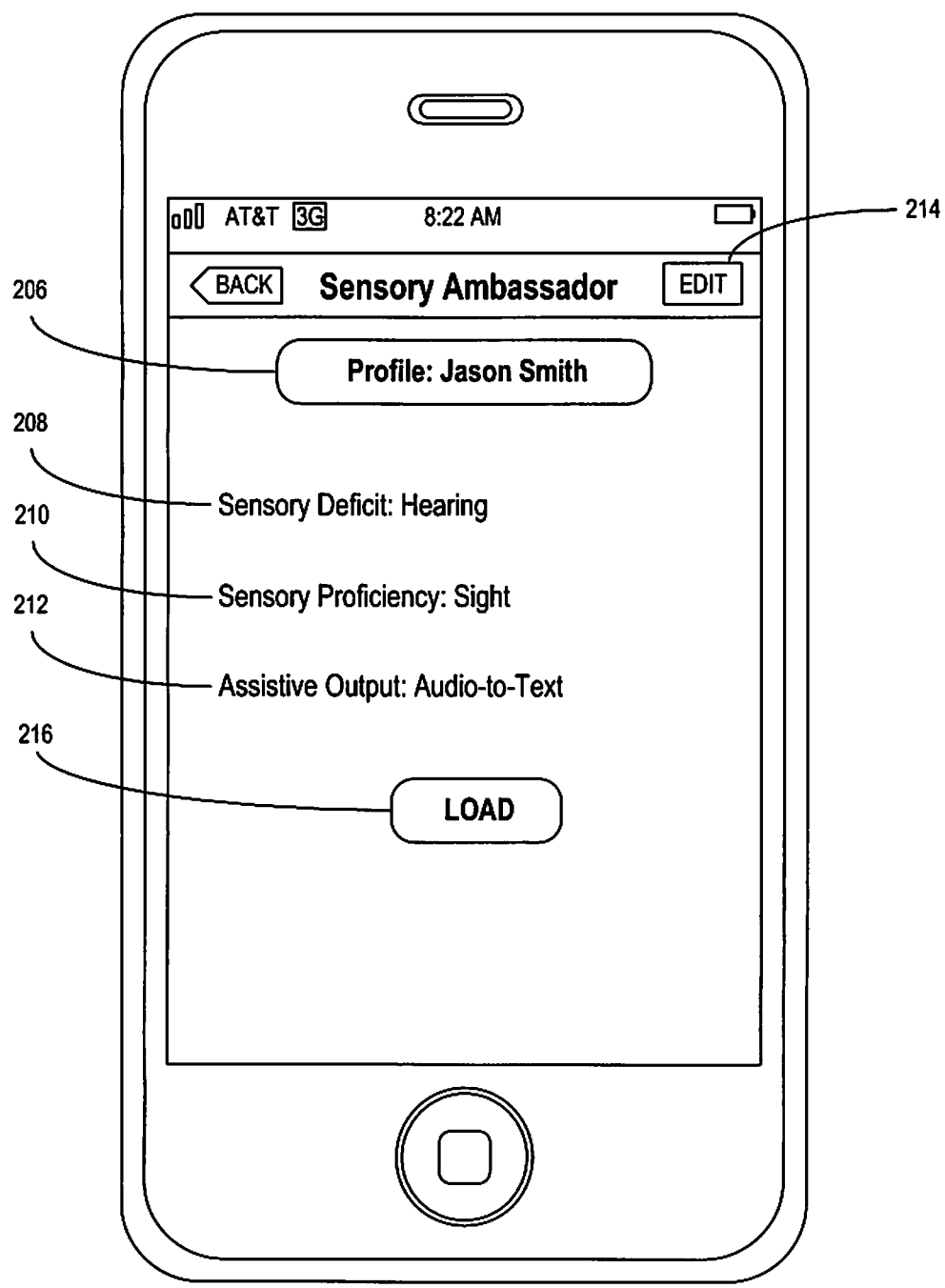
FIG. 9 illustrates a third screen shot associated with the flow chart of FIG. 5.

If the user selects a pre-existing profile or template (block 152), the user may be shown a screen like that shown in FIG. 9 (or screen with comparable functionality), where the user may see the profile name 206, a particular sensory deficit defined for the profile 208, a particular sensory proficiency defined for the profile 210, and a particular assistive output defined for the profile 212. In the upper corner, an "Edit" command 214 may be present so that the user can enter the profile and change one or more parameters associated with the profile. Pre-existing templates may be profiles that are created as a starting point for serving those with particular sensory challenges (e.g., fields pre-populated with information that may be applicable to a user with thermoception dysfunction, to a user with tinnitus and hyperacusis, or to a child user with Sensory Processing Disorder (SPD)).

If the user is satisfied with the current parameters associated with the profile (i.e., elements 206, 208, 210, and 212), the user may select the load command 216 (block 154) in which case the software loads the profile and begins monitoring to see if the criterion is satisfied as described with reference to block 110 of FIG. 5. Alternatively, the user may select the edit command 214 (block 156) in which case the process goes to block 160 of FIG. 7.

Figure 10:
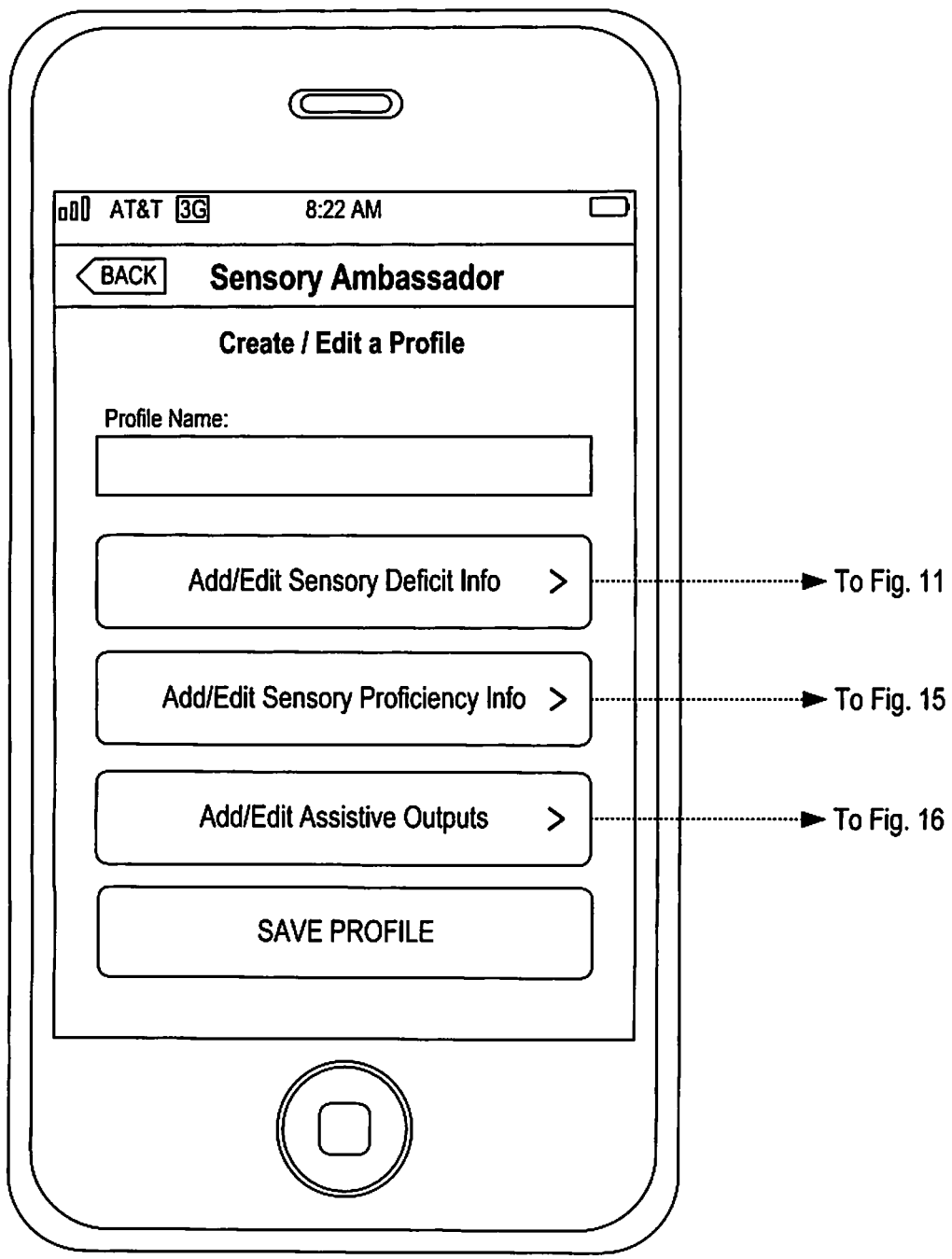
FIG. 10 illustrates a fourth screen shot associated with the flow chart of FIG. 5.

If, instead of loading an existing profile, the user selects the "+" command 204, a blank profile is created (block 158) and the user may see a screen like that in FIG. 10 (or screen with comparable functionality). It should be noted that the edit command 214 and the add new profile command 204 may both take the user to a screen like that illustrated in FIG. 10. If the user is creating a profile, the parameters are blank. However, if the user is editing a pre-existing profile, then the parameters may be pre-populated with information that was previously stored for that profile.

As shown, the screen of FIG. 10 allows for creation of a new profile (and, as noted above, editing of an existing profile is substantially similar, albeit with pre-populated fields). Assuming creation of a new profile, the caregiver may input and save various types of configuration data or parameters in association with the profile, though some software configurations may be pre-programmed or set to "default" values before the caregiver begins this step (i.e., default settings are programmed by the software's manufacturers (this may be particularly true of the templates)). Multiple profiles may be created for one or more disabled individuals (e.g., separate profile names of "Jimmy's Daytime Sensory Ambassador", "Jimmy's Nighttime Sensory Ambassador", and/or "Sally's Sensory Ambassador"), allowing for use of the mobile terminal 10 by different individuals at different times, or the same individual with respect to different profiles, if so desired. The caregiver may utilize a keyboard feature (either hard-wired keys or a virtual keyboard, as with the IPHONE™) to enter such a profile name (block 160). For each profile, the caregiver may also (as illustrated in FIG. 5): (i) add or edit information related to a sensory deficit (block 104) (i.e., for new profiles, sensory deficit information may only be added, whereas for existing profiles, sensory deficit information may be added or edited), (ii) add or edit information related to a sensory proficiency (block 106) (i.e., for new profiles, sensory proficiency information may only be added, whereas for existing profiles, sensory proficiency information may be added or edited), (iii) add or edit assistive outputs (block 108) (e.g., translatory, therapeutic or informative outputs triggered by events detected by the mobile terminal as described herein), and (iv) save a profile.

Figure 11:
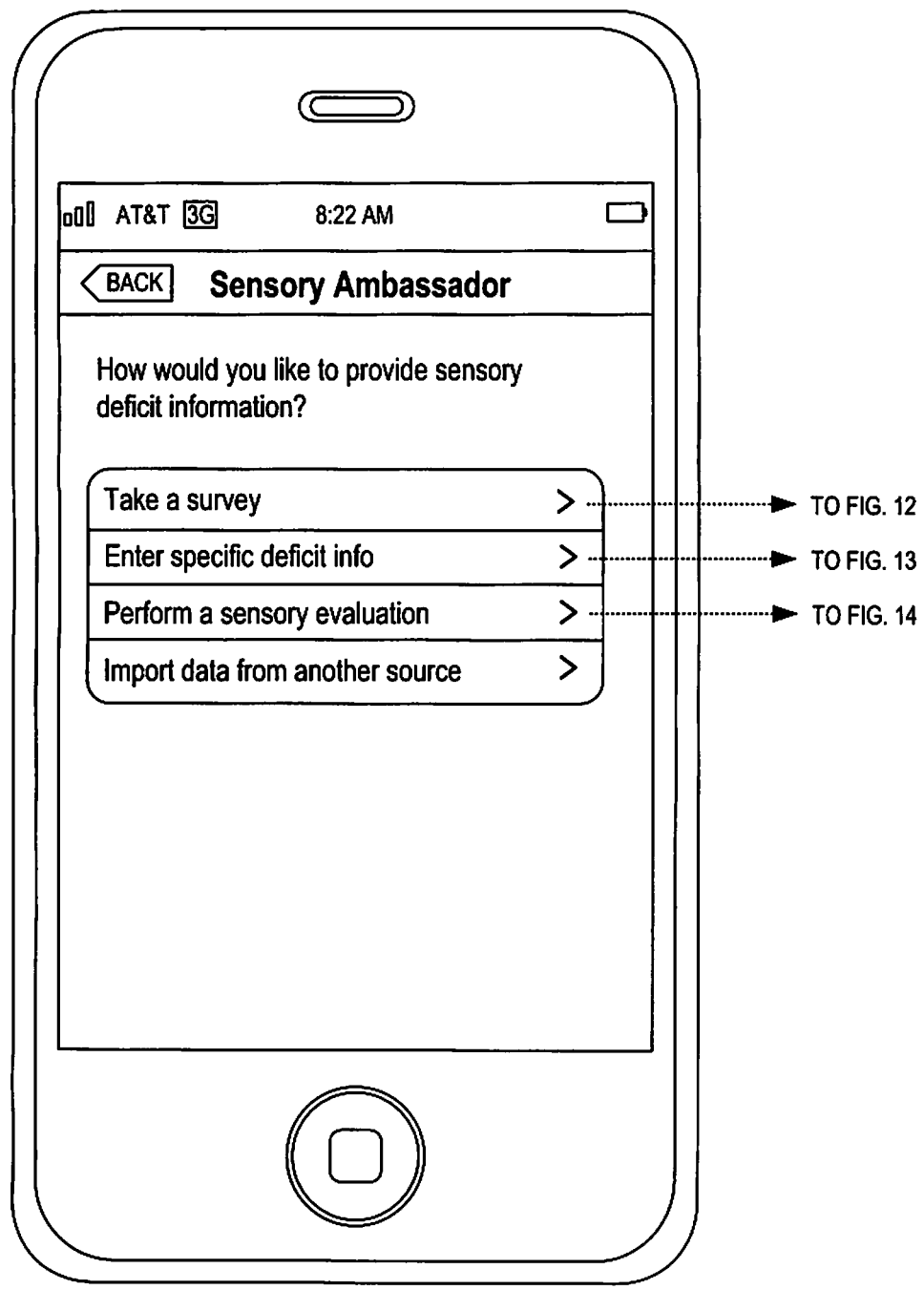
FIG. 11 illustrates a fifth screen shot associated with the flow chart of FIG. 5.

Continuing with the new profile example, and assuming the caregiver has selected the "Add/Edit Sensory Deficit Info" option (FIG. 10), the caregiver may be shown a screen such as that of FIG. 11 (or screen with comparable functionality). The screen of FIG. 11 allows creators of new profiles to choose a manner in which sensory deficit information will be provided. Among the options are: (i) "Take a survey" (e.g., allowing users to answer survey questions as they pertain to the sensory capacities of a particular disabled individual), (ii) "Enter specific deficit info" (e.g., allowing users to provide data or metrics about a specific sensory deficit associated with a user), (iii) "Perform a sensory evaluation" (e.g., whereby tests are performed by the software, in conjunction with sensors of the mobile terminal 10 and/or peripheral devices, to determine sensory deficit information in association with a particular user), and (iv) "Import data from another source" (e.g., allowing users to upload or transfer electronic files containing preexisting sensory deficiency data).

Figure 12:
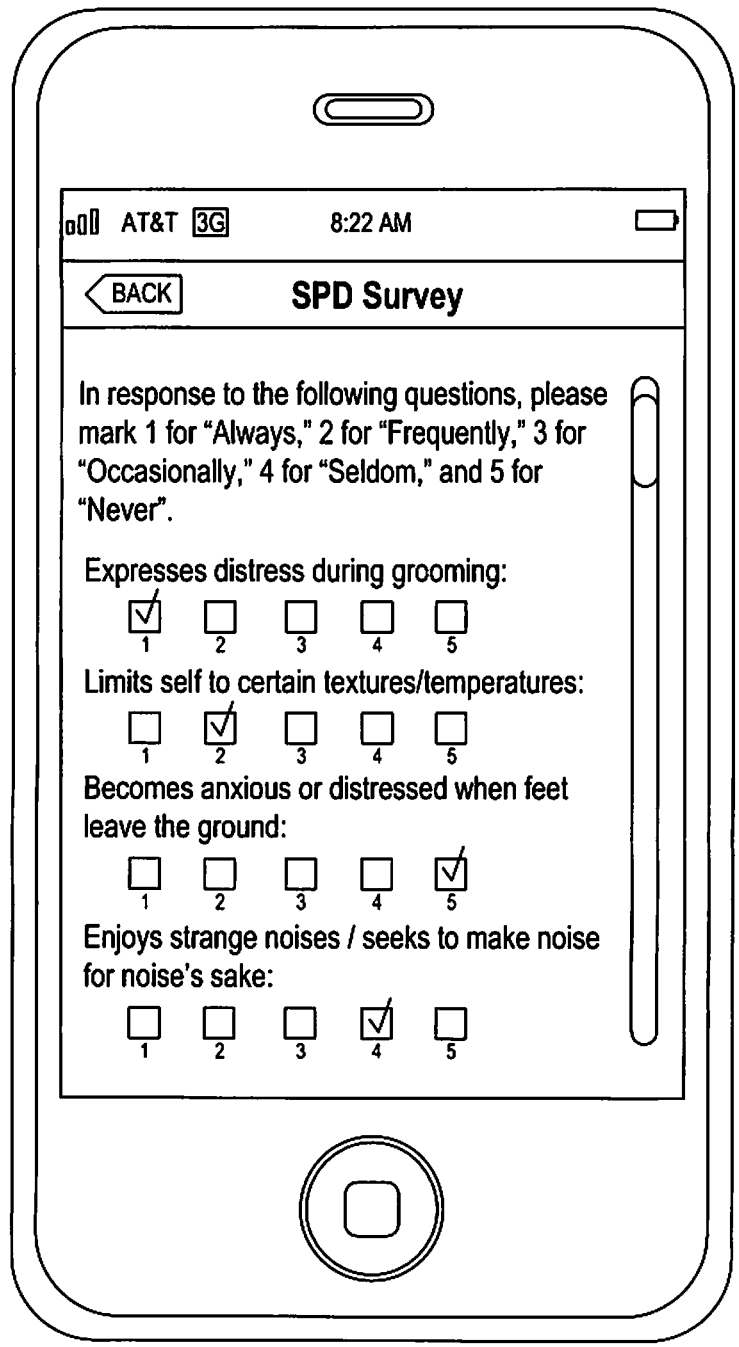
FIG. 12 illustrates a sixth screen shot associated with the flow chart of FIG. 5.

Continuing the example, and assuming the caregiver has selected the "Take a survey" option, a screen such as that of FIG. 12 (or a screen with comparable functionality) may be presented. As shown by FIG. 12, for example, a caregiver may complete an "intake" survey or questionnaire about a child with SPD (i.e., a neurological disability causing difficulties with processing information from the senses), providing information about the child's specific sensory deficits. Such a survey is known in the art as a "Sensory Profile," "Sensory Processing Disorder Survey," or "Sensory Processing Measure Survey," and elements of a prior art survey developed by Winnie Dunn, Ph.D. of the University of Kansas Medical Center may be used for purposes of this disclosure. When completing the survey, caregivers may mark "Always," "Frequently," "Occasionally," "Seldom," "Never" in response to various behaviors associated with a child's tactile sensitivity (e.g., "Expresses distress during grooming"), taste/smell sensitivity (e.g., "Limits self to certain food textures/temperatures"), movement sensitivity (e.g., "Becomes anxious or distressed when feet leave the ground"), sensory-seeking behavior (e.g., "Enjoys strange noises/seeks to make noise for noise's sake"), auditory filtering (e.g., "Is distracted or has trouble when there is lots of noise around"), kinetic energy (e.g., "Has a weak grasp"), visual/auditory sensitivity (e.g., "Covers eyes or squints to protect eyes from light"), etc. When responses to the survey are complete, the caregiver may select a "Save Survey" or similarly labeled option (not shown). As will be described later herein, in some embodiments, survey responses may be used by the software to create or suggest one or more assistive outputs (e.g., a user who always expresses distress during grooming and frequently limits himself to certain textures/temperatures may be oversensitive to tactile stimulation, and so an assistive output may be provided to the user if a tactile stimulation is detected).

Figure 13:
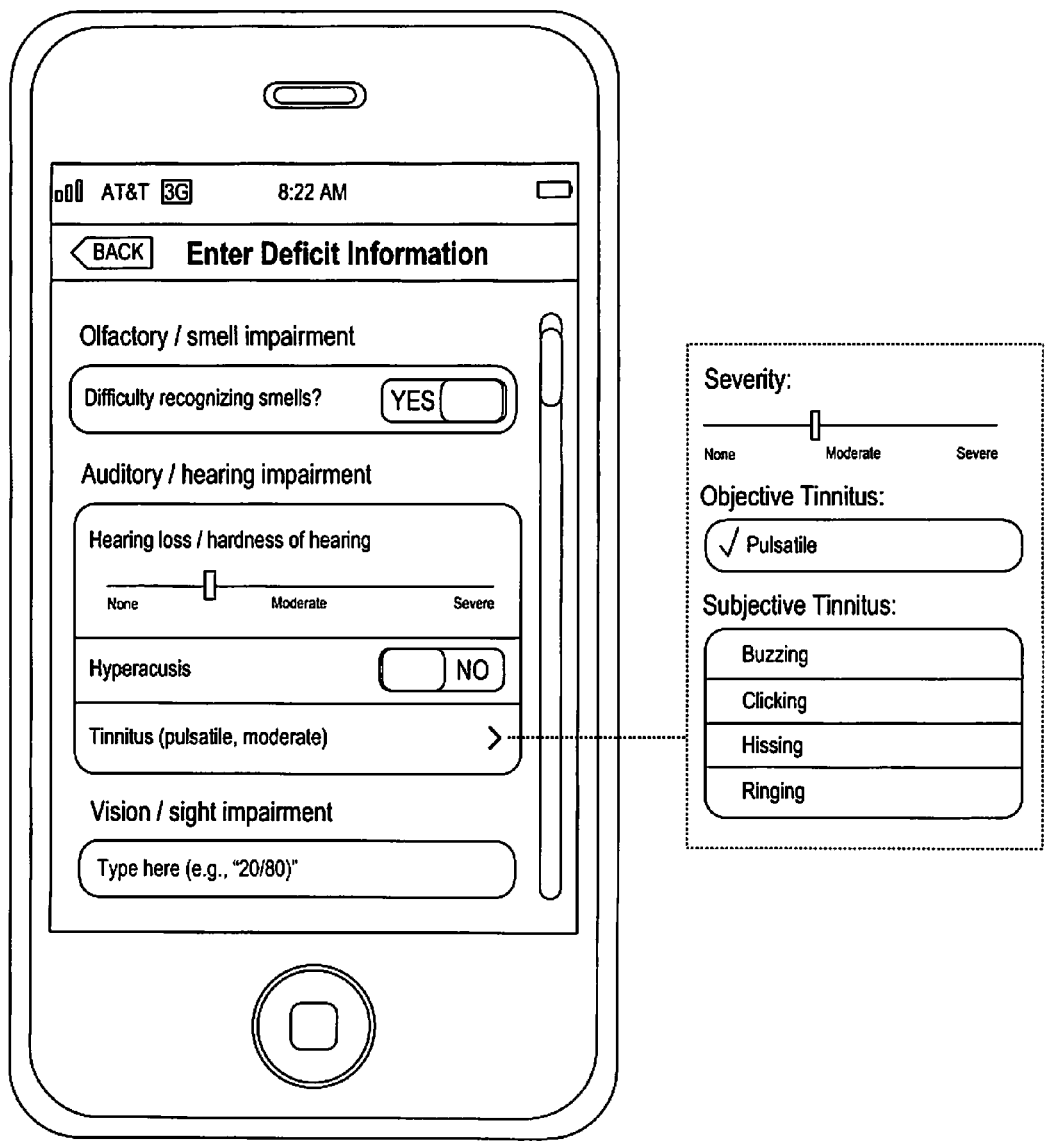
FIG. 13 illustrates a seventh screen shot associated with the flow chart of FIG. 5.

Returning to FIG. 11 and instead assuming the caregiver selects the "Enter specific deficit info" option, one or more screens such as that shown by FIG. 13 (or screen with comparable functionality) may be output. The caregiver may utilize such screens to provide data related to sensory deficits known to be experienced by a particular user of the mobile terminal 10. Such data may be provided using one or more of a variety of different measurement techniques, including: (i) binary measurement (e.g., a user either has an impairment, or does not; for example, a user is hypersensitive to touch and vestibularly hyposensitive), (ii) interval or scaled measurement (e.g., information related to a deficit is entered using a scale such as "1 through 10", "low/medium/high", "always/frequently/occasionally/seldom/never", "severe/mild", "1 through 100%"), (iii) ordinal or ranked measurement (e.g., impairments are ranked in relation to one another, such that a user's tactile hypersensitivity is ranked as a primary impairment, with vestibular hyposensitivity as a secondary impairment, and auditory hypersensitivity as a tertiary impairment; one individual's impairments may be ranked in relation to another individual's, such that a child's auditory filtering capability is in the 37th percentile among all children, or a child ranks "below average" with respect to motion sensitivity), and/or (iv) provision of a specific numeric level associated with a sensory deficit (e.g., "20/80" is entered to describe vision, a frequency range and decibel level are entered to describe hearing loss). For demonstrative purposes, the screen of FIG. 13 shows a mixture of measurement types appearing on a single screen, though in practice, the process for entering specific deficit info may implicate numerous screens, with any or all of the above measurement types utilized in association with any deficit. When the process of entering specific deficit information is complete, the caregiver may select a "Save Deficit Information" or similarly labeled option (not shown).

Figure 14:
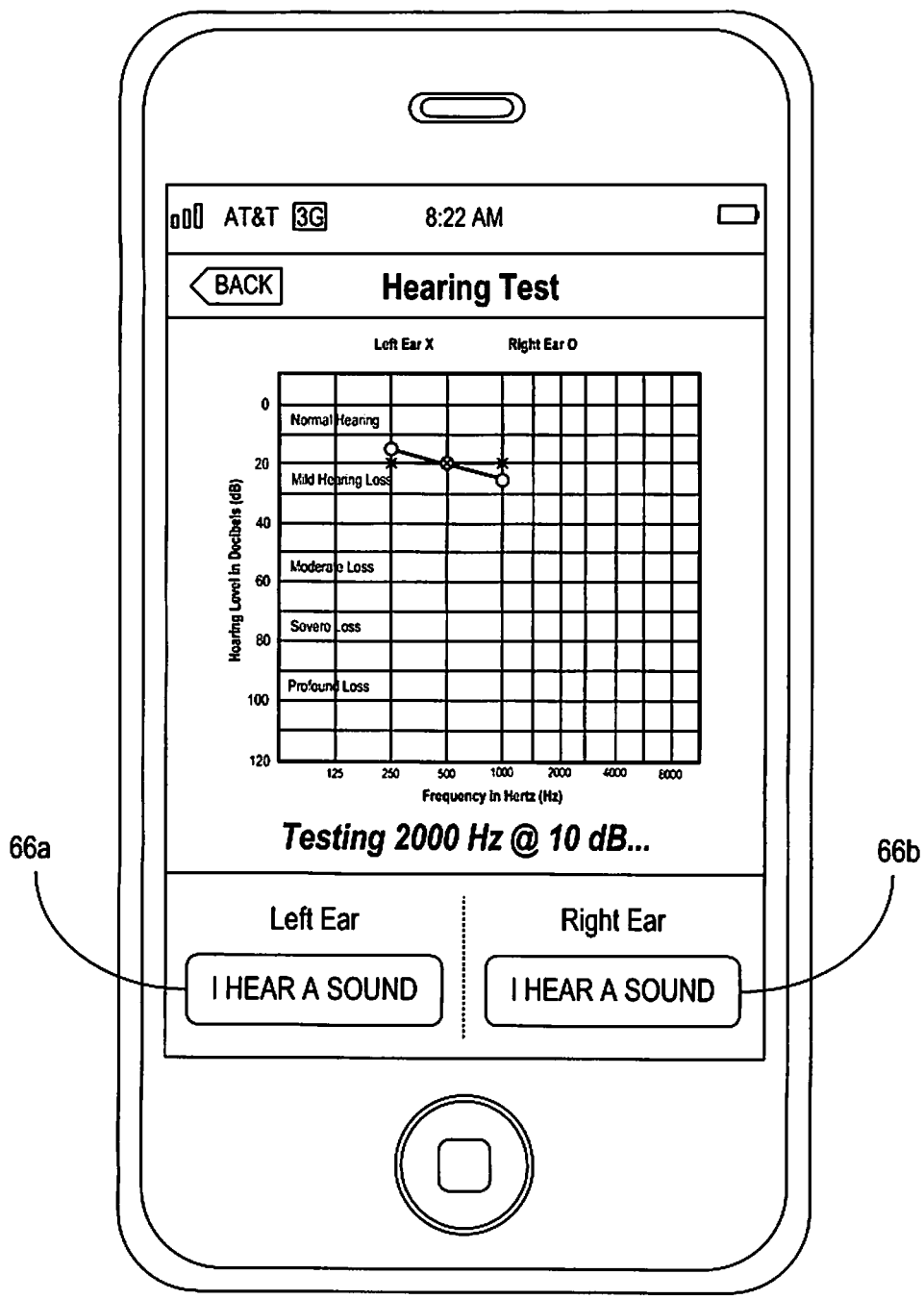
FIG. 14 illustrates an eighth screen shot associated with the flow chart of FIG. 5.

Returning to FIG. 11 and instead assuming the caregiver selects the "Perform a sensory evaluation" option, one or more screens such as that shown by FIG. 14 (or screen with comparable functionality) may be output, allowing a particular user's sensory capacities to be tested or evaluated directly by the software of the present disclosure. For example, using a screen similar to that of FIG. 14, a user's hearing may be evaluated. As is known in the art, a behavioral audiogram may be created, whereby a user's hearing level in association with different frequencies may be measured by the software. For example, tones at different frequencies may each be output at different decibel levels (from quiet to loud), and the user may indicate whether or not he or she can hear the tones as they increase in volume (touch-screen options 66a and 66b may allow for affirmative responses related to the left and right ears, respectively). The result of such a process is the creation of an audiogram for the user, which spells out precisely the deficits (or even proficiencies and hypersensitivities) experienced by the user in terms of hearing (e.g., presbyacusis, or the downward-sloping loss of hearing at progressively higher frequencies, as is common with the human aging process). As described below, such data may be used by the software to create or suggest one or more assistive outputs (e.g., translation of a sound detected at high-frequency, such as a bird call, to a picture output by display screen 16, such as a picture of the bird that emitted the sound). Of course, other senses besides hearing may be so tested by the software. For example, a user's tactile sensitivity may be tested using a series of outputs from a vibration unit (e.g., progressively longer or more forceful vibrations are output, and the user responds affirmatively when the vibrations can be felt by shaking the mobile terminal 10 such that motion is recognized by the accelerometer 34). A user's balance or equilibrioception may be tested using the accelerometer 34 (e.g., an evaluation is administered whereby the user must attach the mobile terminal 10 securely to a belt clip, and then walk a balance beam, with shifts in balance measured by the accelerometer 34 and reported to the software). A user's visual acuity may be tested by (i) projecting a Snellen-scale visual acuity chart onto a wall using a peripheral projection device associated with the mobile terminal 10 (the EXPO™ smartphone by LG ELECTRONICS is an example of a commercially available mobile terminal that employs a projector, in this case a peripheral DLP projection device made by TEXAS INSTRUMENTS CORPORATION), (ii) outputting audio instructions for the user to stand a particular distance from the surface onto which the chart is projected, (iii) outputting audio instructions to read aloud the letters shown on each line of the chart, and (iv) employing a microphone and speech recognition technology to determine whether the user has successfully read the letters of each line (thus determining a level of visual acuity in association with the user). Other sensory capacities may also be tested by the software to the extent possible. Of course, for demonstrative purposes, FIG. 14 shows one example screen for conducting one type of sensory evaluation, though in practice, a variety of screen designs may be employed to accommodate evaluation of a variety of senses, and yet further screens may be designed to facilitate the user's navigation to and from such screens (e.g., after selecting the "Perform a sensory evaluation" option shown by the screen of FIG. 11, a user is then presented with a menu of different evaluation types, from which one may be selected).

Returning again to FIG. 11, a user may select an option to "Import data from another source". Selection of such an option would allow the electronic transfer of preexisting data regarding any sensory deficits associated with a user. In one example, an electronic file may be uploaded locally from the memory of the mobile terminal 10. In another example, a file may be transmitted electronically from another device (e.g., a file is transferred wirelessly from another mobile terminal 10, a file is transferred from a computer 54 to a mobile terminal 10 using a docking station). In yet another example, a file is downloaded from the Internet (e.g., using email, using a Web browser). In this manner, existing spreadsheets, charts (e.g., audiograms), word-processed documents (e.g., Sensory Profiles) or the like may be utilized by the software, rather than having users key-in data that is already documented in some form.

Worth describing at this juncture are some sensory deficit types for which information may be provided. Again, though FIG. 13 shows only a few types of deficits appearing on a single screen, in practice, information for numerous different deficit types may be entered using any number of screens (e.g., a menu system shows categories of deficits, allowing users to drill down from a high level of categorization to provide a more detailed level of information for a particular deficit; for example, a user first selects a "deficits" option, then selects a "hearing" category, then selects "tinnitus," then "objective tinnitus", then "pulsatile tinnitus," and finally enters information about the severity of the particular user's pulsatile tinnitus).

Some users may suffer from a visual impairment or may have difficulty seeing. In one example, a user has a loss of visual acuity (e.g., difficulty seeing clearly, whether shortsightedness, near-sightedness, astigmatism, imbalance of acuity between eyes, or overall lack of acuity or blindness). In another example, a user has a loss of visual field (e.g., a reduction in the total area that can be seen without moving the head or eyes, such as a loss of tunnel vision). In another example, a user suffers from a lack of ocular motor control (e.g., difficulty fixating on objects of particular types or objects in particular locations). In another example, a user has a hypersensitivity to bright environments (e.g., shields eyes in sunlight or when standing in fluorescent light) or to bright colors. In another example, a user is colorblind.

Some users may suffer from a hearing or auditory impairment. In one embodiment, a user has a lost an ability (in part or in full) to hear certain frequencies of sound. For example, a use with mild hearing loss hears only sounds at 25 decibels and above, whereas a user with profound hearing loss hears only sounds louder than 90 decibels. A person's hearing sensitivity in association with particular ranges of frequencies may be plotted on an audiogram, as is known in the art. In another embodiment, a user may suffer from tinnitus, or the perception of sound within the human ear without a corresponding external sound. Tinnitus may be objective (e.g., so-called "pulsatile" tinnitus heard by others, such as a rumbling of blood flow emanating from a vascular source within the body), or subjective (e.g., ringing, buzzing, clicking, or beeping not heard by others). Some users with tinnitus may also suffer hearing loss, and/or may be more sensititive to sounds emitted at certain frequencies (e.g., a particular ringing tone is uncomfortable to hear). Some users may experience hyperacusis (i.e., oversensitivity to certain types of sounds or volume levels).

Some users may experience sensory deficits related to touch. For example, some users may exhibit tactile defensiveness (hypersensitivity to touch). Some users may avoid contact with certain types of textures or objects, such as wool, sand, hair combs, cardboard, or light human touch. In other examples, users may suffer from tactile anesthesia, or inability to register sensation through the skin. For example, a user may have lost, partially or completely, the inability to feel objects using a particular finger or hand.

Some users may experience impairments related to taste (gustatory sensations, as mediated by taste buds). For example, a user may experience ageusia, or the inability to detect sweetness, sourness, bitterness, saltiness in association with foods or beverages. Other users may experience hypogeusia (partial loss of gustatory sensation) or dysgeusia (the distortion or alteration of taste).

Some users may have difficulty smelling or accurately processing olfactory sensations. For example, a user with anosmia may not be able to detect an odor. A user with hyposmia may experience a reduction in the sense of smell (e.g., in association with a particular odor, or with all odors).

Some may perceive odors which are not present (so-called "olfactory hallucinations"), or may be hypersensitive to certain types of odors (e.g., the smell of metal or rubber makes a particular user feel sick).

Some users may experience difficulty sensing temperature. For example, hyposensitive thermoception may result in the inability or impaired ability to register or sense different temperatures (e.g., a user may "under-feel" heat, and so may be prone to kitchen or fireplace burns). Some users may be hypersensitive to temperature (e.g., moderate warmth is perceived as excessive heat; a somewhat cold object is perceived as extremely cold).

Some users may experience problems with balance or equilibrioception. In some examples, balance-related challenges may stem from the vestibular system, resulting in impaired ability to sense body movement, accelerate, or maintain postural equilibrium. Further challenges related to equilibrioception may result in poor coordination, motor planning, or sequencing of actions.

Some users may suffer from challenges related to proprioception, or the ability to interoceptively sense where body parts are located in relation to one another. Some users may experience impairment related to the sensation of joint position, resulting in difficulty determining the location of a body part in space. Some users may experience kinesthetic impairment, resulting in difficulty sensing that a certain body part has moved. Some users with proprioceptive and/or kinesthetic impairments may exhibit clumsiness, insensitivity to pain, or sensory-seeking behaviors (e.g., walk, push objects, write, play with objects, or touch people with excessive force).

Returning to the flowchart of FIG. 5, having already received information about any sensory deficits, the process continues to block 106, wherein information related to sensory proficiencies are received in association with a user. For purposes of this disclosure, a sensory proficiency will be considered a satisfactory level of functioning associated with any of the senses described herein; in other words, if a user doesn't experience a deficit in association with a particular sensory capacity, such a sense may be considered fully functional or proficient.

Given this framework, perhaps the easiest way of receiving information related to sensory proficiencies (block 106 of FIG. 5) may be to first receive information related to sensory deficits (block 104 of FIG. 5), and then infer that all sensory capacities which have not been expressly described as deficient by a user to in fact be proficient. Such an option is presented by the screen of FIG. 15, which allows a user to indicate (using a simple "ON/OFF" switch) that essentially all senses not described as impaired are indeed functioning appropriately. Thus, the user may first provide information related to sensory deficits in a manner similar to any or all of those described with respect to FIGS. 11 through 14, and select this option, such that information related to sensory proficiencies may also be received (i.e., block 106 is complete).

Figure 15:
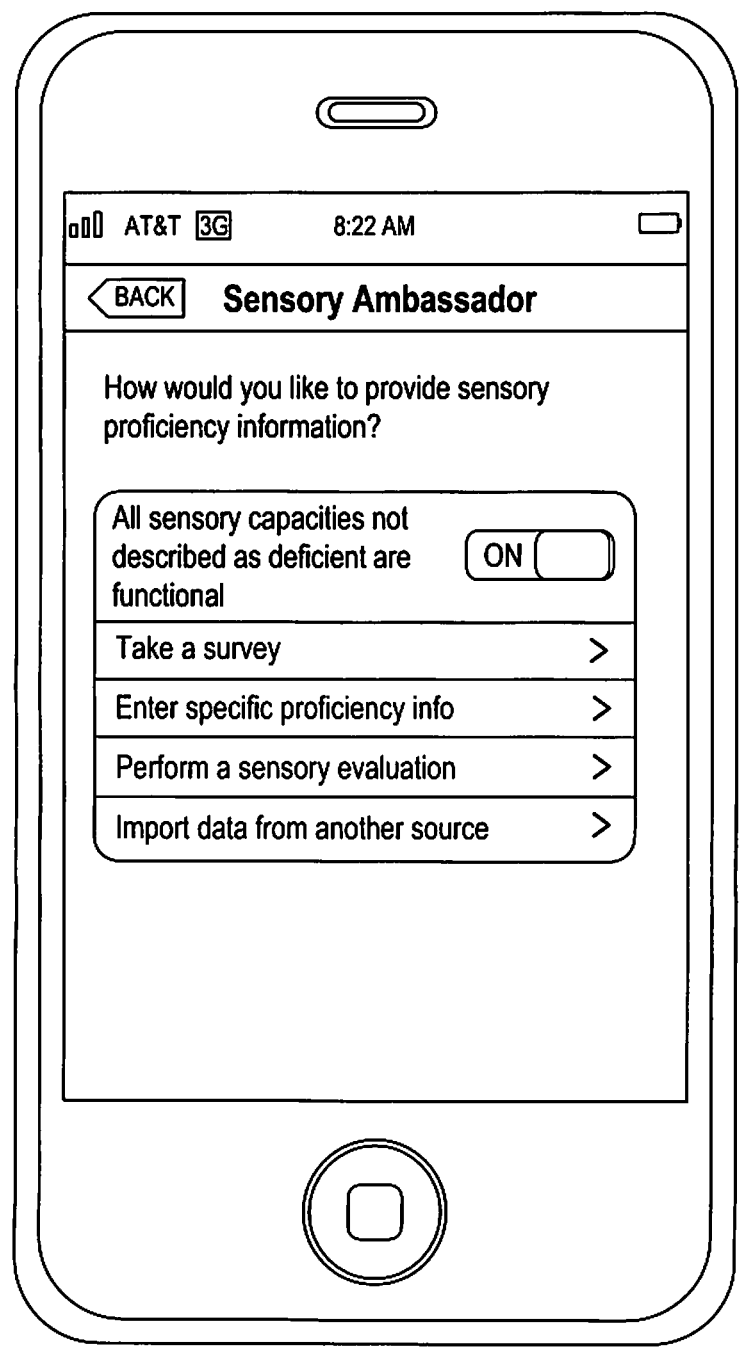
FIG. 15 illustrates a ninth screen shot associated with the flow chart of FIG. 5.

Of course, in some situations, a caregiver or other user may wish to expressly provide information related to one or more functional sensory capacities (e.g., perhaps a particular sense associated with a user is exceptionally well developed, such as acute "20/10" vision). In such a case, a user may first set the switch shown by FIG. 15 to the "OFF" position, and then utilize any of the options shown, including "Take a survey," "Enter specific proficiency info," "Perform a sensory evaluation," or "Import data from another source" (e.g., upon movement of the switch to the "OFF" position, the options are no longer "grayed out" or unavailable as shown by FIG. 15).

Once information related to sensory deficits and proficiencies are received by the software, the process depicted by FIG. 5 continues to block 108, wherein the software stores a criterion for providing an assistive output. A criterion for providing an assistive output may also be thought of as an "assistive output rule," or an instruction which indicates that if an event associated with a sensory deficit is detected, an assistive output based on a sensory proficiency should be provided. Thus, the criteria described herein in essence may serve as "triggers" for the automatic provision of assistive outputs by the software. Two overarching types of such criteria are contemplated: (i) those created automatically by the software in response to receiving sensory deficit and proficiency information at block 104 and block 106 of FIG. 5, and (ii) those programmed explicitly by users of the software. Each type will be discussed in turn.

In some embodiments, software of the present disclosure automatically creates assistive output rules based on sensory proficiency and deficiency information provided by users. For example, sensory proficiency and deficiency data associated with a user may be organized into a database (an example database is described below), and the database may be scanned by the software. The purpose of the scan may be to identify trends within the data that would suggest certain types of assistive outputs may be beneficial to the user. For example, programmed logic within the software code may indicate that assistive output rules are to be automatically created when certain fields within the database indicate certain data. For example, if one or more database records associated with a user's visual acuity describe vision as proficient, and yet other records indicate the user suffers moderate to severe hearing loss at high frequencies (4000 Hz and above), a rule may automatically be created whereby sounds (detected by integrated microphone 26 or clip-on microphone 58e) occurring above 4000 Hz are automatically "translated" into images and output via display screen 16 (e.g., a chime from a clock is detected, and so a picture of a clock is output by the screen). Other examples of assistive output rules are described below, but suffice it to say that any rule may be so created by the software upon analyzing data provided by users; through time and experience, creators of the software may learn that users with particular deficits commonly program certain assistive output rules, and such information may feed the software's logic for automatically creating assistive output rules.

In other embodiments, assistive output rules may be created by users of the software. Turning to FIG. 10, such a process may begin when a user selects an "Add/Edit Assistive Outputs" option. The user may then be brought to a screen similar to that shown by FIG. 16. An assortment of assistive output rules is shown. In this example, we assume some rules have been created automatically by the software and others have been programmed by a user. The rules include: "Translate high-frequency audio to pics" (e.g., created automatically by the software to translate high-frequency sounds to images), "Put sunglasses on when it's too bright" (e.g., created by a caregiver to help manage a user's hypersensitivity to light), "Rule 1 (11/15/10 4:57 pm)" (e.g., a rule set by a caregiver but not expressly labeled, and so automatically given a label based on the time and date at which it was created), "Calming audio for nervous arm-flapping" (e.g., created by a caregiver to output soothing music and instructions via speaker 14 or headphones 58f if a user's arms are flapping repeatedly as detected by an accelerometer in ring 58d or in the mobile terminal 10; a disabled individual whose arms are flapping may be engaged in proprioceptive self-stimulatory behavior as a coping mechanism for sensory overstimulation of some kind), "Rule 2 (11/23/10 6:18 am)" (e.g., again, not labeled by a caregiver), "Convert pictures to touch-screen Braille" (e.g., an object detected by integrated camera 24 or peripheral camera 60 is identified using an online image-comparison database communicatively coupled to the software via an API, such that a text-based description of the object may be output by display screen 16 as a sequence of vibrations representing Braille characters), and "Balance therapy after falling down" (e.g., created automatically by the software such that if a user with known equilibrioceptive challenges falls down (as detected by accelerometer 34), a balance-related game may be output via display screen 16, as a tool to help the user stand back up). Some of these example assistive output rules will be described in more detail below. It is possible that the screen of FIG. 16 may instead show (i) no rules (i.e., none have yet been created) or (ii) categories of rules (i.e., such that users may organize rules by type). To continue the example, it is assumed that the user selects the "+" option shown at the top-right of the screen, so as to create a new rule.

Figure 17:
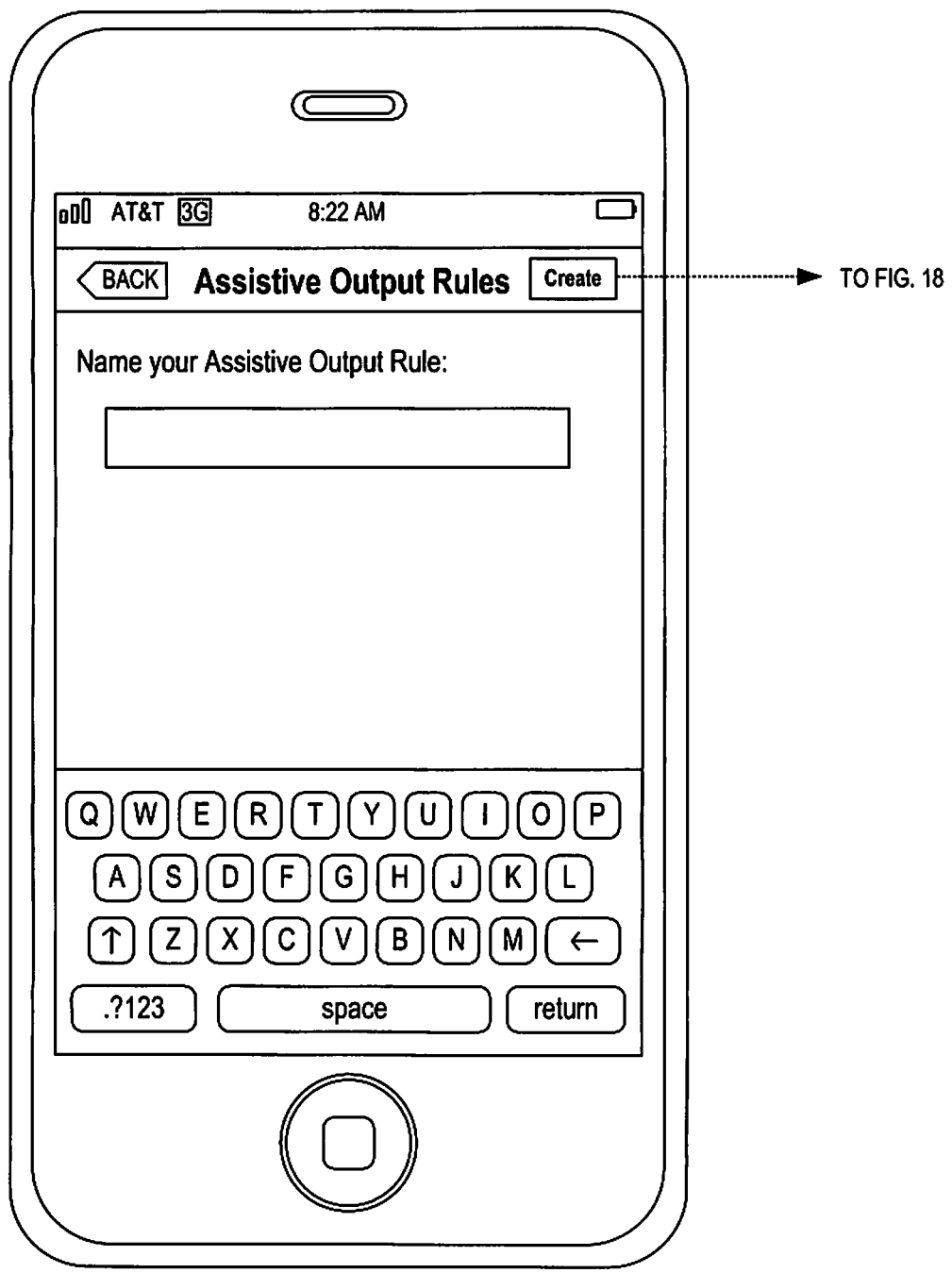
FIG. 17 illustrates an eleventh screen shot associated with the flow chart of FIG. 5.

FIG. 17 illustrates a first example screen for configuring a new assistive output rule, in which the user is given the option to label the rule, such as by typing a name in the space provided. If the user chooses not to exercise this option and simply presses "Create," a timestamp type label may be supplied as described above.

Figure 18:
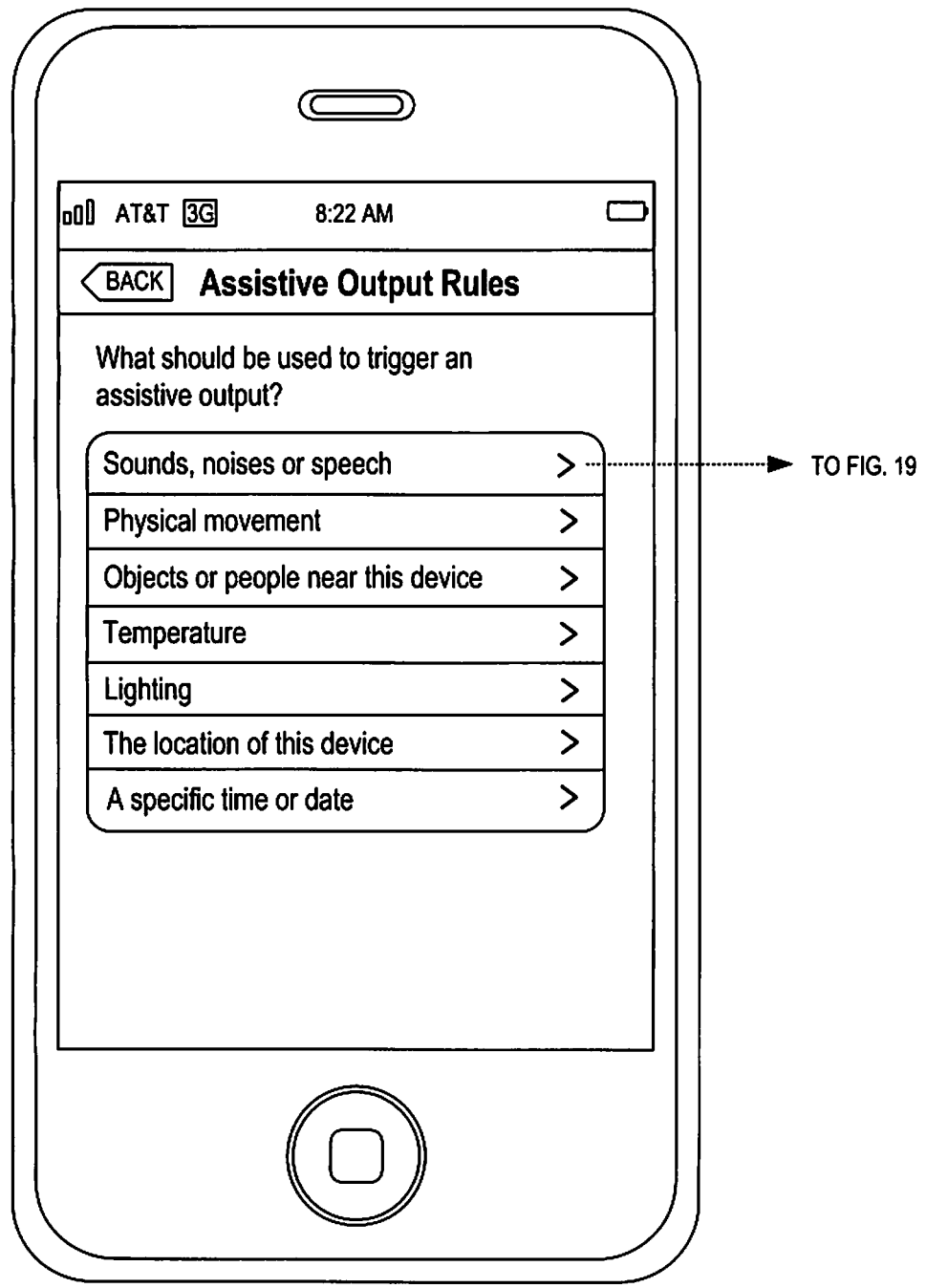
FIG. 18 illustrates a twelfth screen shot associated with the flow chart of FIG. 5.

Once the user selects "Create," a second screen for configuring an assistive output rule may be presented, an example of which is shown by FIG. 18 (or one of comparable functionality). Using a screen such as this, the user may first choose a broad type of criterion ("trigger") to be further considered (at block 110 of the flowchart of FIG. 5, as described below) in determining whether an assistive output should be provided. Several categories of criteria are presented (though others may be used): "Sounds, noises or speech"; "Physical movement"; "Objects or people near this device"; "Temperature"; "Lighting"; "The location of this device" and "A specific time or date". These categories are examples; other categorizations, subcategories, and navigational techniques (e.g., "searching" instead of browsing) may be employed to help a user specify a type of assistive output rule he or she would like to create.

Figure 19:
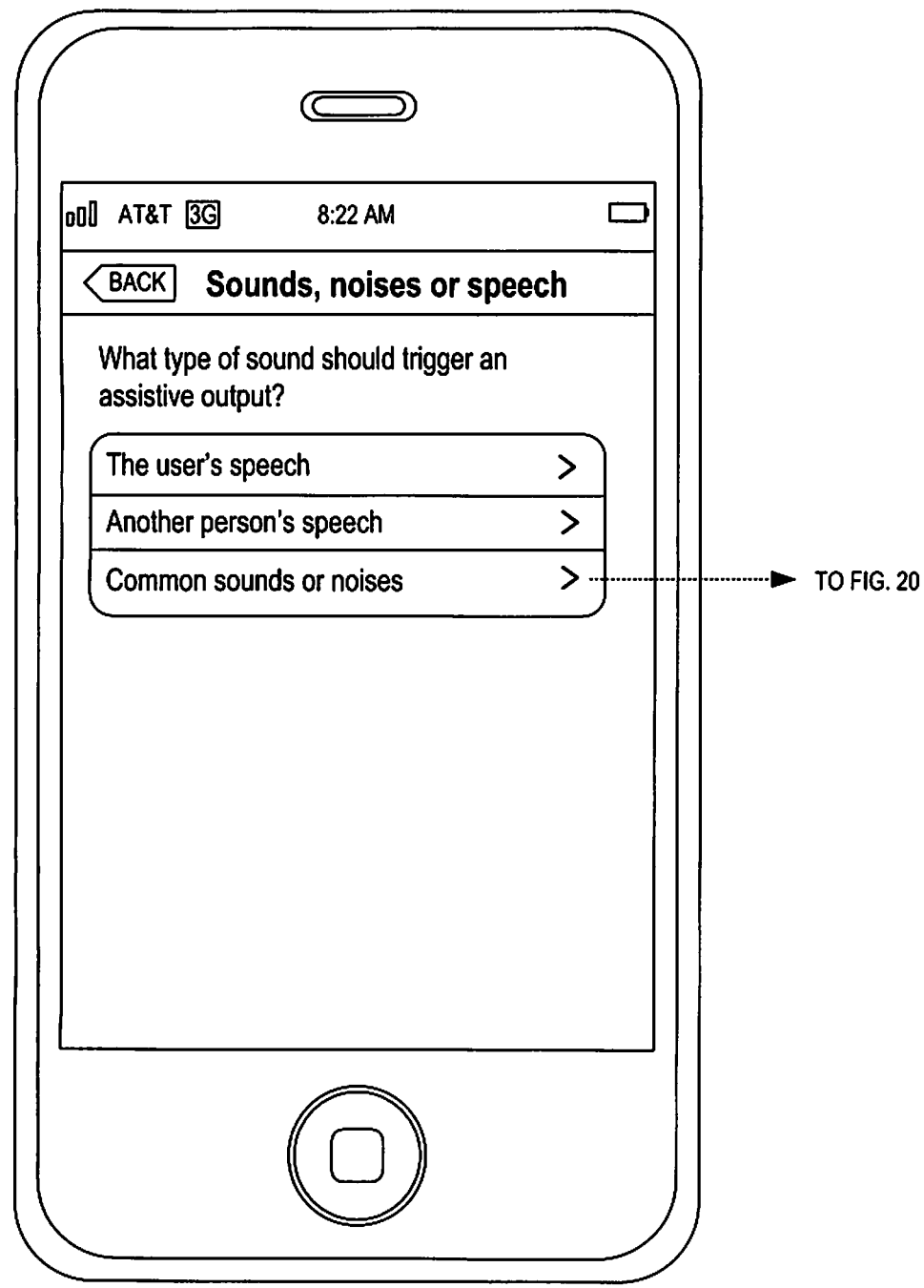
FIG. 19 illustrates a thirteenth screen shot associated with the flow chart of FIG. 5.

For example, assuming the user selects the option labeled "Sounds, noises or speech," a screen such as that of FIG. 19 (or one of comparable functionality) may be presented, where various subcategories may help the user refine the description of a type of detected audio that should be used to trigger an assistive output. As shown, subcategories include "The user's speech," "Another person's speech," and "Common sounds or noises". Continuing the example, it is assumed the user selects "Common sounds and noises," resulting in the output of a screen such as that shown by FIG. 20 (or one with comparable functionality).

Using a screen such as this, the caregiver may begin to configure a criterion such that an identified sound (i.e., as detected by integrated microphone 26 or clip-on microphone 58e) will be used to trigger an assistive output. Using one option, a user may search or browse an already-existing "Library" to select a particular sound to be used as a trigger. Using another option, the user may choose to record and save a custom sound.

Figure 21:
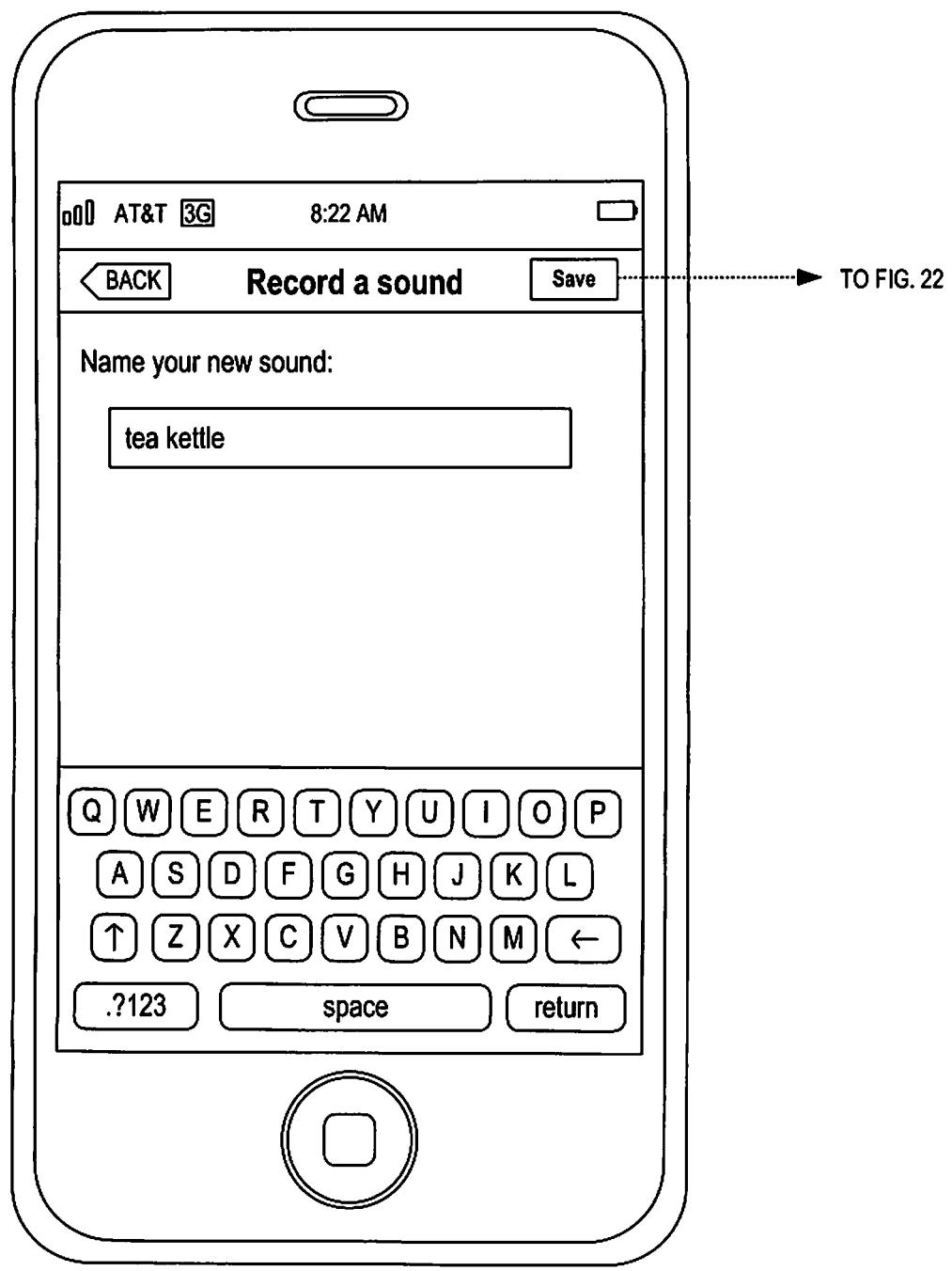
FIG. 21 illustrates a fifteenth screen shot associated with the flow chart of FIG. 5.

If the caregiver selects the latter option, a screen such as that of FIG. 21 (or one with comparable functionality) may be shown, enabling the user to enter a name for the new sound (e.g., "tea kettle"). After the user selects the "Save" option shown by FIG. 21, a screen such as that of FIG. 22 (or one with comparable functionality) may be output.

Figure 22:
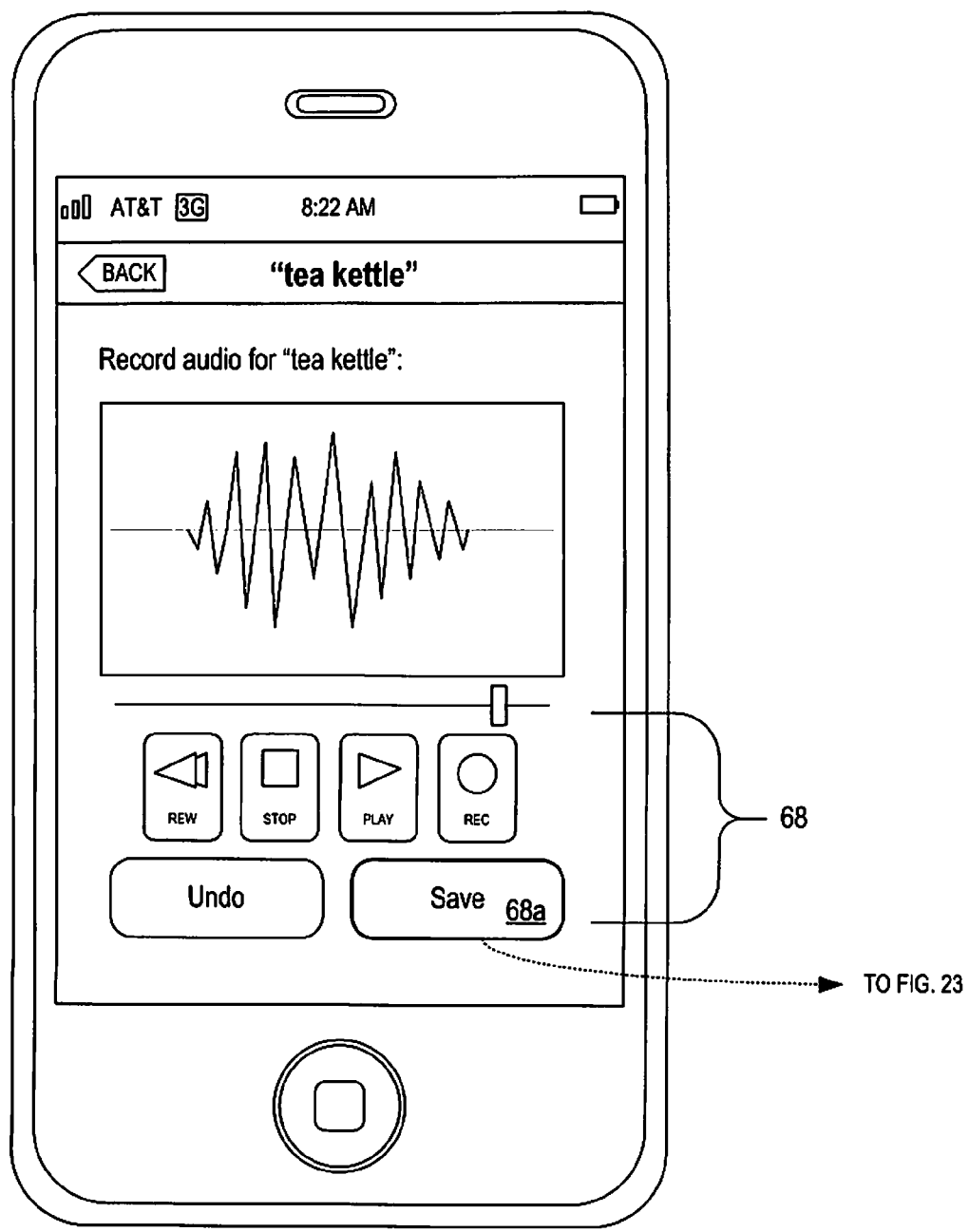
FIG. 22 illustrates a sixteenth screen shot associated with the flow chart of FIG. 5.

The screen of FIG. 22 allows a user to record and save a customized sound (in this example, the sound emitted by a particular tea kettle once water boils). Controls 68 allow the user to Rewind, Stop, Play, Record, Skip (to a particular point within a recording), Undo and Save. Audio may be recorded by an integrated microphone 26 of the mobile terminal 10, by a clip-on microphone 58e, or by another microphone in communication with the mobile terminal 10 or computer 54. Once a sound is saved (control 68a), an electronic file (i.e., digital audio waveform) may be added to the software's internal library (such that the sound can be later discovered using the search and browse mechanisms shown in FIG. 20). Sound recognition functionality as it pertains to computer 54 and mobile terminal 10 is well known in the art, with sophistication and accuracy improving over time. For example, U.S. Pat. No. 6,990,445 to Ky describes a method of identifying a detected audio waveform using a database of prerecorded audio waveforms; this document is hereby incorporated by reference for all purposes. WINDOWS MEDIA® PLAYER as developed by MICROSOFT CORPORATION employs a form of audio waveform matching termed "advanced audio fingerprinting," to identify digital audio files by comparing them within a database of known files. In another example, using tools readily available in the APPLE® IPHONE™ software development kit, NUANCE COMMUNICATIONS, INC have developed a software application for the IPHONE called DRAGON DICTATION. The application allows users of the IPHONE™ to dictate common speech; the speech is then recognized so as to produce (i) text (e.g., saved to a notepad) or (ii) a command to execute a particular software function. Similar techniques may be utilized to detect sounds and speech for purposes of the present disclosure.

Continuing with the example and assuming the user has selected the "Save" control 68a, the user has now specified a criterion (i.e., the detection of a sound produced by a tea kettle) for the provision of an assistive output. To complete programming the assistive output rule, the user may now define the assistive output that should be produced should the criterion be satisfied. To do so, one or more screens such as that of FIG. 23 (or one with comparable functionality) may be utilized.

Figure 23:
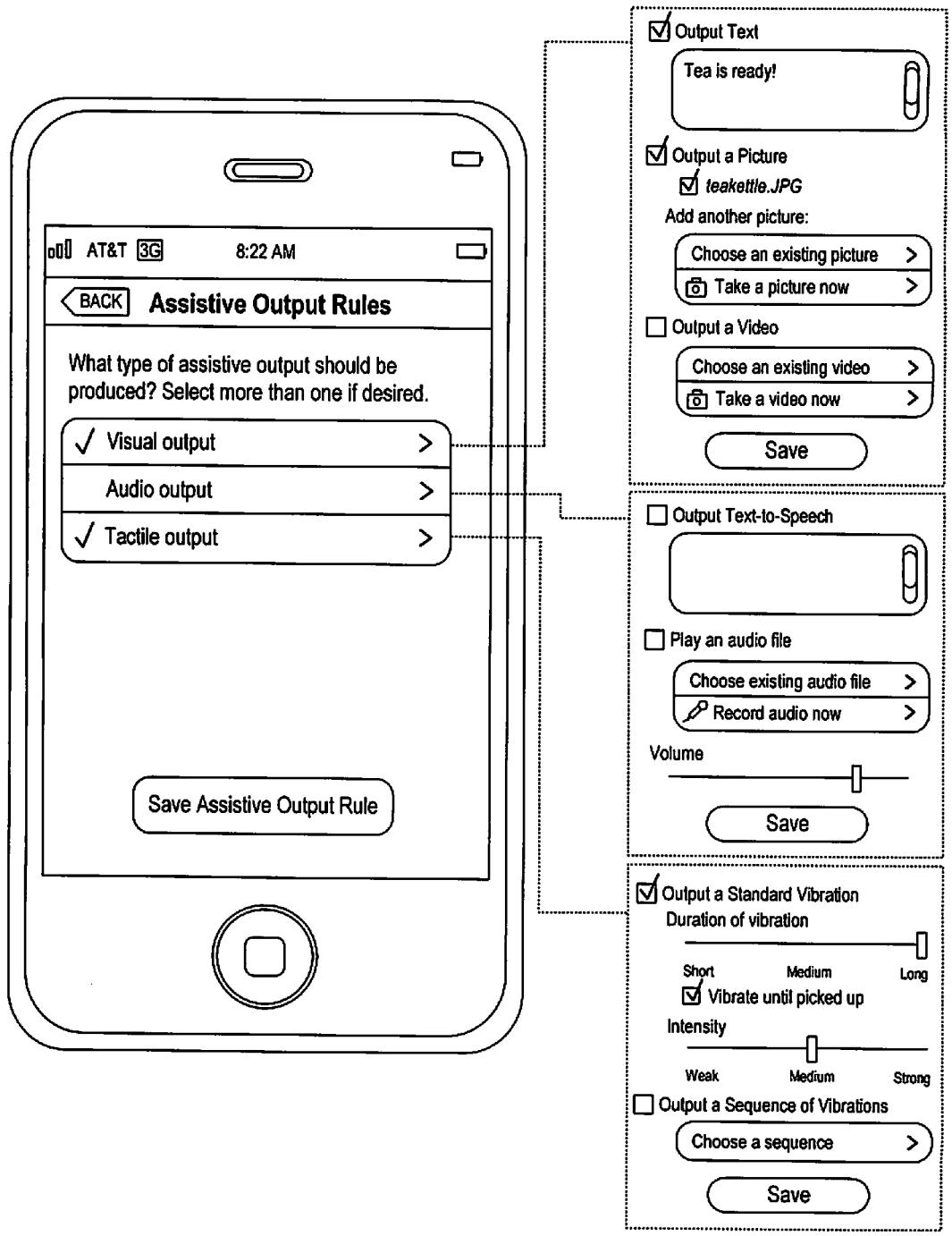
FIG. 23 illustrates a seventeenth screen shot associated with the flow chart of FIG. 5.

The user may then select one or more types of assistive outputs, including but not limited to: (i) visual outputs, (ii) audio outputs, and (iii) tactile outputs (e.g., a vibration). As shown by FIG. 23, the user has selected "Visual output," which may allow (e.g., through one or more subsequent screens) the user to configure various media which should be presented by the display screen 16, including: (i) text (e.g., as shown, a user can select an option to add text, and type any desired text into a provided field), (ii) one or more static images (e.g., a single picture output for a period of time, two pictures output simultaneously, three pictures output in sequence, etc.), (iii) one or more videos (e.g., as shown, a user can select an existing video, such as one stored in the memory of the mobile terminal 10, or record a new video using an integrated or peripheral video camera), (iv) combinations of the above (e.g., a picture with a text caption underneath instructing the user to perform the action shown in the picture). It should be understood that a variety of configurations and preferences may additionally be specified by users at this time, even if they are not explicitly illustrated by FIG. 23. For example, the user may additionally configure: (i) sequences for presenting different visual media as part of an assistive output (e.g., a second picture should appear 10 seconds after a first picture), (ii) the location or size of pictures, text or video on a screen when an assistive output is produced (e.g., a picture should appear underneath a video); (iii) specific display devices other than screen 16 which should be utilized in conjunction with the assistive output (e.g., a second display screen or peripheral projection device associated with the mobile terminal 10 should alternately or additionally be utilized). Finally, the user can select an option to "Save" any configured visual outputs, as shown.

If the user were alternately or additionally to select the "Audio output" option of FIG. 23, an assistive audio output may be configured and saved. Configuration choices may include: (i) a Text-to-Speech (TTS) option, allowing a user to type text which will then be "read aloud" by a computerized voice when the assistive output is executed; (ii) an option to load a saved audio file (e.g., a song file saved in a common format such as MP3, WAV or AAC; a voice recording; a sound effect; etc.) or record a new audio file (e.g., using an integrated or peripheral microphone; and (iii) an option to adjust the volume associated with an audio output. Further configuration options (not shown) may allow for multiple types of audio to be played simultaneously or in sequence, using one or more peripheral speakers or a peripheral headset, and so on.

If the user were alternately or additionally to select the "Tactile output" option of FIG. 23, an assistive vibratory or tactile output may be configured and saved. Configuration choices may include: (i) an option to output a standard vibration (e.g., using an integrated vibration unit of the mobile terminal 10), including sub-options to configure the length and intensity of the vibration (e.g., the user configures a "medium"-intensity vibration that is to last until a user picks up the mobile terminal, as detected by a sensor); and (ii) an option to output a sequence of vibrations. For example, a disabled end user may be blind or have significantly impaired vision. A caregiver may, before transferring the mobile terminal 10 to the disabled individual, select an option to output a sequence of vibrations of different intensities used to represent one or more conventional Braille characters. As an example of the representation of two-by-three Braille dot matrices on a touch-screen device, using the NOKIA 770 INTERNET TABLET, which features a piezoelectric material built into the touch screen that vibrates when an electric signal is applied to it, the scientists at the University of Tampere in Finland created software that represents a raised dot within a Braille matrix as a single pulse of intense vibration, and an absent dot within a Braille matrix a longer vibration made up of several weaker pulses. Other methodologies of representing Braille using a touch screen may be so employed. Further, other three-dimensional objects (e.g., words, pictures) may be represented using a touch-screen associated with mobile terminal 10, using other techniques. For example, as described in U.S. Patent Application No. 2009/0174673 to Ciesla, cavities associated with touch-screen buttons may be inflated and deflated by a pump coupled to a fluid reservoir, in subsets or individually, to provide three-dimensional tactile guidance to a user interacting with a touch-screen; this document is hereby incorporated by reference for all purposes.

Figure 16:
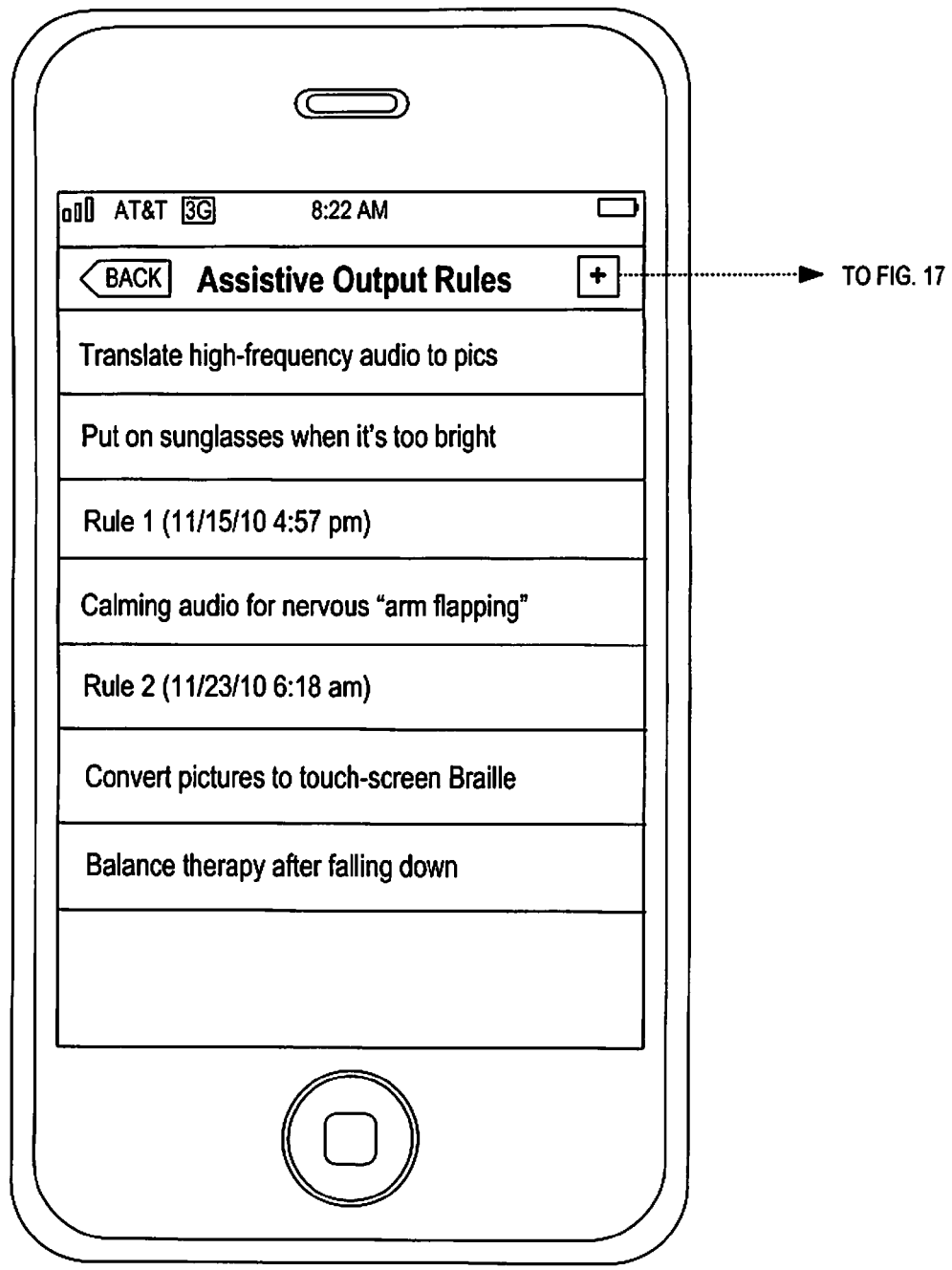
FIG. 16 illustrates a tenth screen shot associated with the flow chart of FIG. 5.

After configuring such preferences, the user selects the "Save Assistive Output Rule" option such that the new rule is created and added to the list of saved rules shown by FIG. 16. A variety of rules catering to a variety of sensory deficits may be programmed in this manner.

With the rule now programmed, the process depicted by the flowchart of FIG. 5 continues to decision block 110, wherein it is determined whether the criterion saved in association with the rule has been satisfied. If the criterion is satisfied—e.g., a specified event has occurred, such as an utterance of a particular word or phrase, or increase in ambient light as detected by a light sensor—the process continues to block 112, wherein the assistive output is provided. If the criterion is not satisfied, the process loops at decision block 110 (notwithstanding other instructions saved in association with an assistive output rule, the software continually determines whether criteria are satisfied).

A variety of sensors, peripherals, peripheral devices, and other technologies associated with the mobile terminal 10 may be employed when determining whether a specified event has occurred. Some examples will now be set forth in which particular technologies are paired with the detection of particular behaviors, environmental changes or properties, occurrences, and the like. Though an example is not provided for every possible pairing, this should not be construed as limiting the capacity of the software to employ all available technologies in detecting whether criteria have been satisfied.

In some embodiments, a criterion may be satisfied if a sound, a noise or human speech is detected. Either or both of an integrated microphone 26 and a peripheral microphone, such as clip-on microphone 56e, may be employed to help detect such audio occurrences. In one example of detecting speech, an integrated microphone 26 is used to detect that a particular word or phrase has been spoken. In another example, a clip-on microphone 56e is used to detect the word or phrase. In any case, an uttered word or phrase may be "matched" to a voiceprint (or waveform) stored within electronic memory. The voiceprint may be generic (e.g., the speech criterion is satisfied the word or phrase may be spoken by any person), or associated with a particular person (e.g., the speech criterion is satisfied only if the word or phrase is spoken by a particular person). Various technologies for so-called biometric voiceprint matching using mobile terminals are known in the art (e.g., the PHONEFACTOR system manufactured by PHONEFACTOR, INC of Overland Park, Kans. utilizes such technology). Of course, other sounds besides speech may be detected (e.g., human sounds such as crying or screaming, animal sounds such as a dog's bark or a bird's chirp, sounds occurring in an urban environment such as a car's horn, sounds occurring at home such as those emitted by home appliances). In one example, as described, an audio waveform detected by a microphone may be matched to a prerecorded waveform for purposes of identifying the detected waveform, using technologies similar to those incorporated by reference above. In some embodiments, a database of sounds may be stored locally by the mobile terminal 10. In other embodiments, a central server may store a database of sounds, and the mobile terminal 10 may communicate with such a database for the purposes of identifying detected sounds. One such database is maintained by COMPARISONICS® CORPORATION of Grass Valley, Calif. Another such system, the SOLAR (Sound Object Localization and Retrieval) system as developed by researchers at the University of Illinois at Champagne-Urbana, compares sounds detected by microphones to a vast database of sound types, so as to distinguish car horns, dog barks, trains, human voices, etc. Software of the present disclosure may communicate with such a database using an API. In some embodiments, in order for a criterion to be satisfied, noise must be above a threshold decibel level (e.g., as specified by a user). In another embodiment, for a criterion to be satisfied, a sound must occur a certain number of times within a specified time period (e.g., a repeated sound suggests a user may be engaged in auditory sensory-seeking behavior).

In some embodiments, a criterion may be satisfied if physical movement is detected. In some embodiments, physical motion is associated with a user of the mobile terminal 10. For example, certain bodily motions performed by a user may be detected using peripheral devices 58*a-f*. In one example, an arm flapping motion is detected through the employ of ring 58*d*, watch 58*c* or other peripheral device attached to an arm. Waving of the hand, punching and hitting may be so detected. In one embodiment, covering of the ears or eyes may be detected using a combination of sensors (e.g., eyeglasses 58*a* and ring 58*d*), with such actions suggesting the user may be engaged in sensory-avoidant behavior (e.g., the environment is too bright or too loud for the user to effectively process). In another example, a peripheral anklet may transmit data to the mobile terminal 10 that suggests the user may be running, kicking, or shaking his or her leg. In another example, rocking in place or shaking of the head are detected using eyeglasses 58*a* (e.g., a motion sensor, infrared sensor, RFID transponder, or other sensor is embedded within the eyeglasses, communicating relative head position to the mobile terminal 10). In one example, eyeglasses 58*e* are used to determine that the user's gaze is oriented toward the mobile terminal (e.g., using camera 60, an RFID transponder, an infrared sensor, or the like). In another example, a separate peripheral device associated with an object, person or area (e.g., an RFID receiver or other sensor placed in a particular location) may be used in conjunction with eyeglasses 58*e* (e.g., worn by a disabled individual) to determine that a disabled individual's gaze is indeed oriented in the direction of the object, person or area (e.g., for at least a threshold percentage of time during a particular time period); for example, if a user's gaze is affixed in a direction away from a source of light, sound, or other stimulus, it may be determined that the user is engaged in sensory-avoidant behavior.

Further, in some embodiments, any of the above motions may be detected without the use of a separate peripheral device. For example, an integrated camera 24 or motion sensor may detect motion activity (e.g., as facilitated by the hanging of mobile terminal 10 around a user's neck using lanyard 62, or by the attachment of the mobile terminal 10 to a belt clip, the sensor is oriented to detect activity motion activity occurring in front of the user). In some embodiments, motion must last for a predetermined duration, or occur at a particular velocity, for a criterion to be satisfied. Accelerometer 34 and/or an integrated altimeter may detect the mobile terminal 10 (and perhaps thus its user) has fallen to the ground. Also, direct physical interaction with the mobile terminal 10 may be considered. For example, a pressure sensor associated with a button or screen of the mobile terminal 10 may detect an excessive amount of force, an accelerometer 34 may detect excessive motion, or a light sensor may detect a pattern indicative of tactile sensory-seeking behavior (e.g., the light sensor is repeatedly covered and uncovered). In another example, a user repeatedly attempts to lower the volume associated with speaker 14 or a peripheral headset, suggesting auditory overstimulation. In some embodiments, combinations of several of the above behaviors may lead the software to conclude that criteria have been satisfied. For example, simultaneous crying above a threshold decibel level and physical mishandling of the mobile terminal 10 are illustrative of tactile sensory-seeking. In another example, tactile interaction with the mobile terminal 10 is first detected (e.g., using a pressure sensor), and then accelerometer 34 determines the device has been dropped or put down, suggesting tactile avoidance.

In some embodiments, the detection of a nearby person or object may satisfy a criterion. In one example, such a person or object may wear or carry a device equipped with a sensor, and the sensor may in turn communicate the presence of the object or person to the mobile terminal 10. For example, one or more sensors or other technologies associated with a first mobile terminal 10 (e.g., carried by a disabled individual) may be used to determine that a second mobile terminal 10 or peripheral device (e.g., carried by another individual) is present. Many technologies may be employed to accomplish such a goal, including a motion sensor, infrared sensor, RFID, GPS, triangulation of geolocation using WiFi or cellular network nodes. In one such embodiment, a first and second mobile terminal 10 may be registered (e.g., using software of the present disclosure) as "buddy" or "friend" devices (e.g., to facilitate the determination that a specific person or "friend" is nearby a disabled individual at a particular time). In another embodiment, a microphone may be used to detect a voiceprint associated with another person (e.g., a specific caregiver) or sound associated with a particular object.

In another embodiment, an optical camera, such as an integrated camera 24, or a camera associated with a peripheral device, such as camera 60, may be used to detect the presence of a particular person or object. Either or both of a still camera and video camera may be so utilized, and such cameras may capture images periodically, continuously, upon demand of a user, or in response to instructions stored within the software (e.g., an instruction states to actuate a camera in response to a loud spike in ambient volume as detected by a microphone). For example, image comparison search may be employed, allowing for images captured by a camera to be matched with those included within a database. In one embodiment, the database is stored locally. For example, a user takes a digital photograph and stores it within memory of the mobile terminal 10, such that a camera may capture a new image and compare it to the stored digital photograph (e.g., if a match is detected, a criterion is satisfied). In another embodiment, the database is maintained by a central server communicatively coupled with the mobile terminal 10. An example of a large online database of images used for image-comparison purposes is the TINEYE REVERSE IMAGE SEARCH ENGINE created by IDEE, INC of Toronto, Canada, which includes a commercial API allowing third party software applications (such as the software of the present disclosure) to communicate with the database. In this manner, captured images may be analyzed to detect particular objects or people, and such detection may satisfy a criterion related to an assistive output rule. For example, the detection of a fire or stove may be beneficial to a person with a thermoceptive deficit, the detection of a dog may be beneficial to someone with a known tactile hypersensitivity to fur, the detection of a flower may be beneficial to someone with a poor sense of smell, or the detection of a particular type of food may be beneficial to someone with an impaired gustatory sense. Again, effective positioning of the mobile terminal and/or its peripherals may assist in such detections; for example, a peripheral camera 60 must be oriented outward from the user for objects in front of the user to be detected.

In some embodiments, an optical camera associated with mobile terminal 10 may be used to recognize text, and a criterion may be satisfied upon the detection of text (whether any text, or a specific word or phrase). For example, Optical Character Recognition (OCR) technology may be used to identify letters. Methods for using OCR technology are well known in the mobile terminal art. For example, a user with a NOKIA phone (such as the N95) running the SYMBIAN operating system may take advantage of the NOKIA MULTISCANNER OCR feature, pointing the phone's optical camera at physical text, such that the text is recognized by the phone's software and output via the phone's display. Recognized text may then be saved, and the language library used to help identify words may be updated over the air. Such technology may be employed to assist a user with a vision deficit, who may encounter objects with physical text in his or her natural environment (e.g., books, signs, etc.), but may be challenged or unable to read such text.

In some embodiments, the detection of a specific amount of light in the environment proximate to the mobile terminal 10 may satisfy a criterion. For example, a light sensor may detect a particular abundance or lack of light during a period of time (e.g., indicating that the mobile terminal is in direct sunlight, or in a dark environment).

In some embodiments, the detection of a specific environmental temperature may satisfy a criterion. For example, a thermometer may be used to determine that the mobile terminal is in a particularly cold environment (e.g., beneath 40° F.). In another example, a directional temperature sensor may determine that a nearby object is at or above a threshold temperature (e.g., a nearby stove, fire, or other object is excessively hot). In another example, a Really Simple Syndication (RSS) feed may be monitored such that weather trends associated with the mobile terminal's current environment are known.

In one embodiment, the detection of an altitude or altitude change may satisfy a criterion. For example, an altimeter may be used to determine that an altitude associated with the mobile terminal has dropped rapidly within a short period of time. In another embodiment an altimeter may detect that the mobile terminal 10 is currently at a high altitude, which in and of itself may affect the sensory capacities of a user.

In one embodiment, the detection of a barometric pressure or change in barometric pressure may satisfy a criterion. For example, a barometer detects a change in atmospheric pressure, which satisfies a criterion.

In some embodiments, data concerning the geographic location of the mobile terminal 10 may satisfy a criterion. As is known in the mobile terminal art, a current geographic location may be determined using GPS technology, triangulation using WiFi or cellular network nodes, or the like. In one example, a criterion may be satisfied if the mobile terminal 10 is within proximity of a particular geographic location at a particular time. In another example, a criterion may be satisfied if the mobile terminal 10 has strayed outside of a geographic "safe zone" expressly programmed by a user (e.g., a 10 mile radius surrounding school and home). In another example, a criterion is satisfied if the mobile terminal 10 has been detected within sufficient range of three separate geographic areas within a particular time (e.g., a child carrying the mobile terminal has gone from school, to an after school program, and finally to home on a particular afternoon). In another example, a criterion is satisfied if the mobile terminal 10 has been taken to a "new" geographic location as per a database storing previously visited locations. In another embodiment, using GPS, WiFi triangulation, and/or cellular triangulation, the current location of a mobile terminal 10 is determined to be in an area characterized by particular sensory properties (e.g., a bus station is loud and dark; a library is quiet and bright; an amusement park implicates vestibular stimulation, a beach is hot, wet, bright and sandy; etc.).

In some embodiments, a property or state associated with a user's body (e.g., a biometric reading), or a change associated therewith, may satisfy a criterion. For example, a change in a user's heart rate or other property may suggest the user is nervous or excited, which in conjunction with another occurrence (e.g., a loud noise), may suggest that the user is struggling with sensory regulation. In some embodiments, a criterion is satisfied based on heart rate data associated with a user of the mobile terminal 10. For example, a user's heart rate may be monitored through the employ of a patch 58*b*, wristwatch 58*c*, ring 58*d*, or other wearable device that may detect and transmit such data (e.g., a bracelet, anklet, wristband, etc.). A criterion may be satisfied by a specified increase in, decrease in, or consistent level of beats per minute (e.g., a user's heart rate remains beneath 60 beats per minute for a period of time). In some embodiments, a criterion is satisfied based on blood pressure data associated with a user of the mobile terminal 10. For example, a user's blood pressure may be monitored through the employ of a patch 58*b*, wristwatch 58*c*, ring 58*d*, or other wearable device, such as an armband. A criterion may be satisfied by a specified increase in, decrease in, or consistent level of pressure (e.g., a user's blood pressure spikes above 130/80). In some embodiments, a criterion is satisfied based on body temperature data associated with a user of the mobile terminal 10. For example, a user's body temperature may be monitored using a peripheral device described herein (e.g., a patch 58*b*, wristwatch 58*c*, or ring 58*d* comprising an infrared or heat sensor). A criterion may be satisfied by a specified increase in, decrease in, or consistent body or skin temperature. In some embodiments, a criterion is satisfied based on electrodermal or galvanic skin response (GSR) data associated with a user of the mobile terminal 10. Such data are used in the art to monitor and infer human emotions (e.g., fear, anger, anxiety, startle response, orienting response). GSR data may be read and transmit using a peripheral device, with the device enabled to measure electrical resistance between two points on the user's skin. Commercially available sensors such as the GSR 2™ as produced by THOUGHT TECHNOLOGY LTD of Plattsburgh, N.Y. may be adapted for purposes of this disclosure. A criterion may be satisfied based on an increase or decrease in electrodermal activity (e.g., a sharp increase may suggest a user has grown fearful, anxious or disoriented).

In some embodiments, a criterion may be satisfied based (in part or in whole) on the occurrence of a particular time or date. For example a caregiver who knows that a user with SPD is scheduled to attend occupational therapy on Wednesday at 4:30 p.m. might create an assistive output in conjunction with this occasion. In one example, the assistive output occurs before the occasion, to prepare the user mentally for the upcoming experience (e.g., a display screen reads, "Almost time for OT! Remember, one leg at a time when you're on the ropes!" and presents a picture of a rope ladder). In another example, a specific time frame is set (e.g., Wednesday between 4:30 and 4:40), such that if a criterion is satisfied during the specified time period, an assistive output should be produced (e.g., if a camera detects a trampoline during the time period, or an accelerometer detects a bouncing motion during the timer period, a previously recorded video of the user successfully jumping on the trampoline is output via display 16, to model to the user an appropriate behavior when using the trampoline). In other words, in some embodiments, both (i) a criterion related to input from a sensor and (ii) a time/date criterion must be satisfied for an assistive output to be produced. An internal clock or calendar coupled to CPU 28 may assist with the determination of a current time and/or date.

Having described a wide array of criteria that may trigger an assistive output, and manners for detecting the satisfaction of such criteria, the discussion now turns to block 112 of the flowchart of FIG. 5, wherein an assistive output is provided. As described previously with respect to FIG. 23, a user programming an assistive output selects one or more desired output types (e.g., text and a vibration), and any content associated therewith (e.g., types in and saves a block of text to be output). Thus, the assistive output as configured by the user in block 108 of FIG. 5 is now initiated in block 112.

Generally speaking, certain communication types of assistive outputs may make particular sense when matched to certain sensory deficits and proficiencies received in blocks 104 and 106 of FIG. 5 (e.g., for a user with a hearing deficit and visual proficiency, audio is converted to text; for a user with tactile hyposensitivity and auditory proficiency, sensory-seeking interaction with the mobile terminal involving excessive force may be discouraged with an audio instruction). Rather than walk through each possible arrangement, four particular examples will now be described wherein a user programs criteria for an assistive output, the criteria are satisfied, and the assistive output is produced as instructed.

Figure 20:
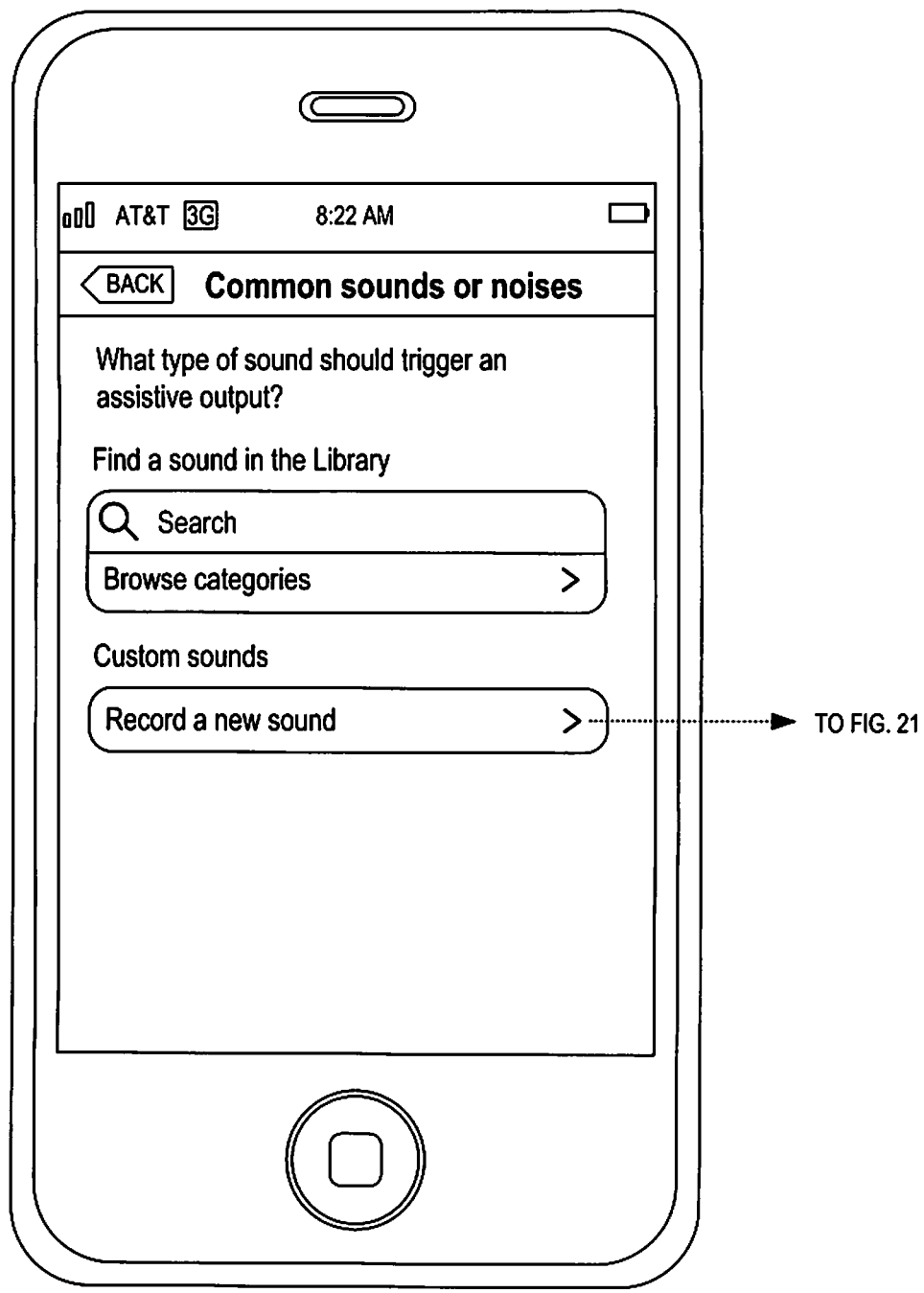
FIG. 20 illustrates a fourteenth screen shot associated with the flow chart of FIG. 5.
Figure 24C:
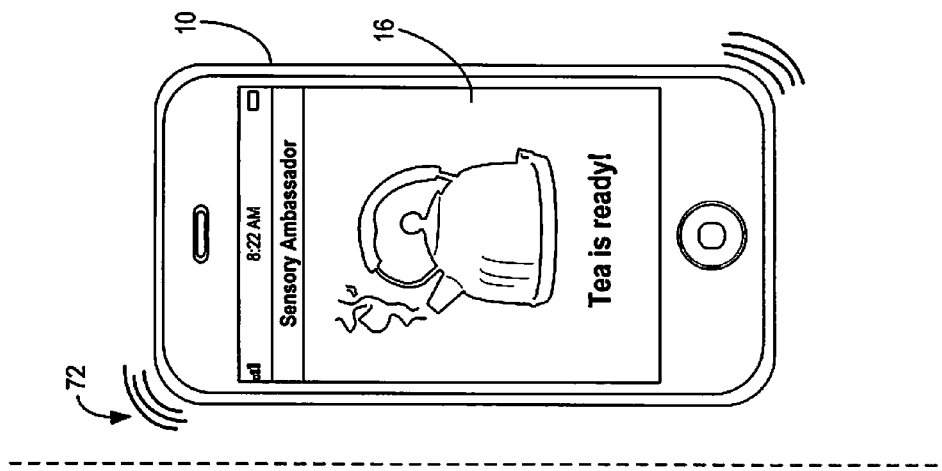
FIGS. 24A-C illustrate an eighteenth, nineteenth, and twentieth screen shot associated with the flow chart of FIG. 5, as well as a peripheral device which may interface with a mobile terminal, and an object which emits a sound that may be detected by the peripheral device.
Figure 24B:
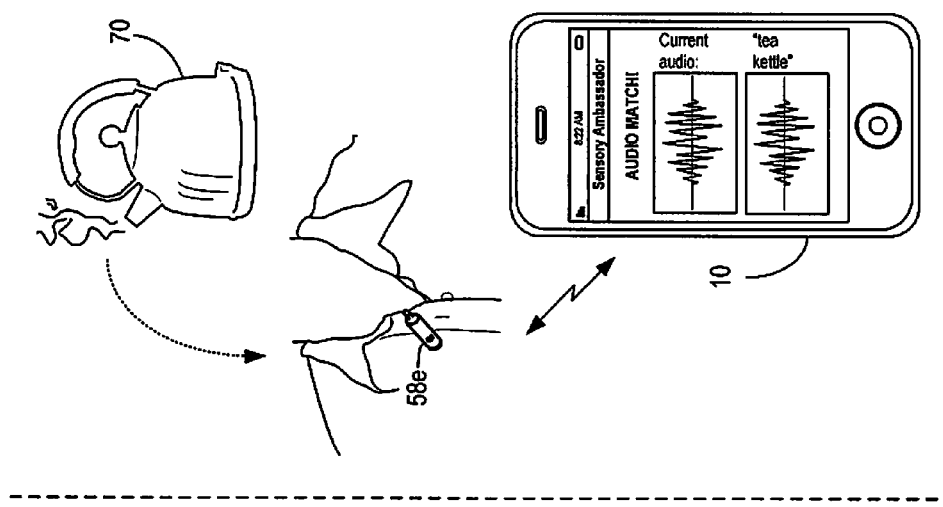
Figure 24A:
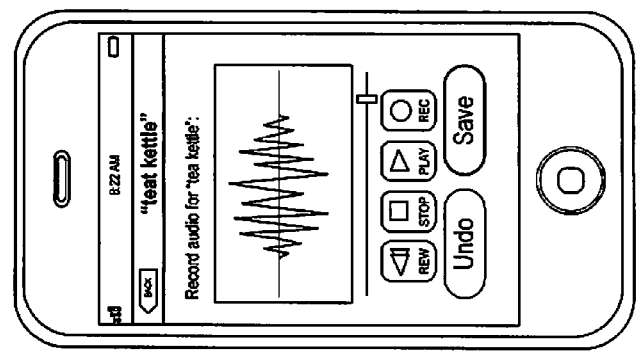

In the first example, illustrated by FIGS. 24A-C, a user with a hearing deficit is prompted with a visual and tactile output upon detection of an audio event. In this particular example, a user has saved an electronic file capturing the audio that should be used to trigger the assistive output; as in FIG. 20, FIG. 24A shows a screen whereby the user records and saves a noise associated with a tea kettle. In FIG. 24B, clip-on microphone 58e picks up the sound emitted by the tea kettle 70, such that software of the present invention (operating on mobile terminal 10) detects a "match" between the detected sound and the previously recorded audio waveform. Of course, microphones other than clip-on microphone 58e may be so utilized (e.g., integrated microphone 26, or another type of peripheral microphone communicatively coupled to the mobile terminal 10). Turning to FIG. 24C, as a result of the detection of the audio event, an assistive output is produced, comprising: (i) a visual output of screen 16, including a picture of the tea kettle 70 and text indicating "Tea is ready!" (i.e., as programmed using the screen of FIG. 20), and (ii) the actuation of a vibration unit to stimulate the user's sense of touch (illustrated by motion marks 72).

Figure 25C:
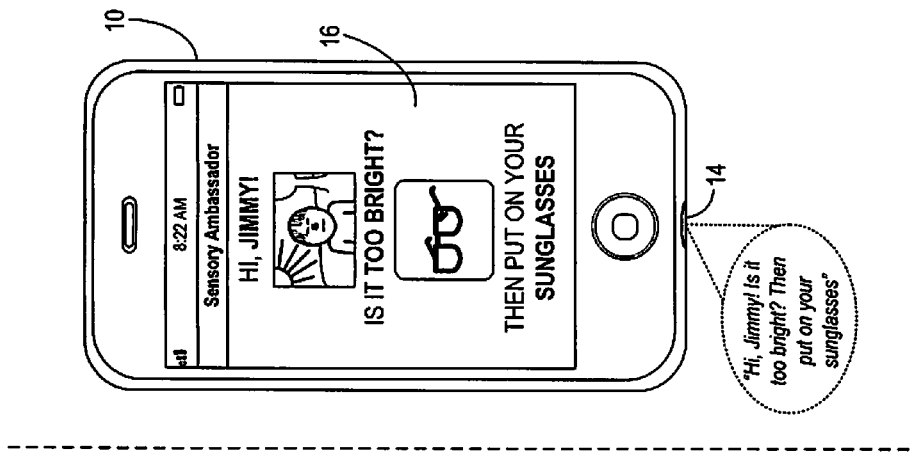
FIGS. 25A-C illustrate a twenty-first, twenty-second, and twenty-third screen shot associated with the flow chart of FIG. 5, as well as an environment surrounding the mobile terminal.
Figure 25B:
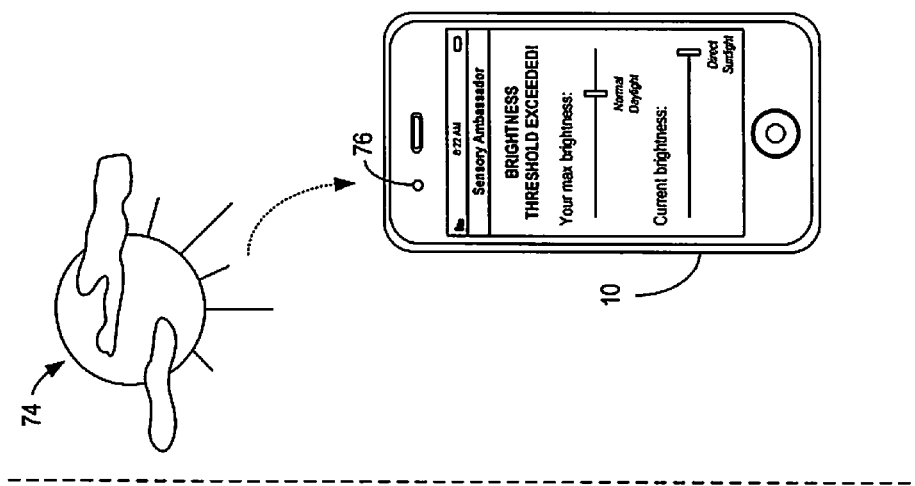
Figure 25A:
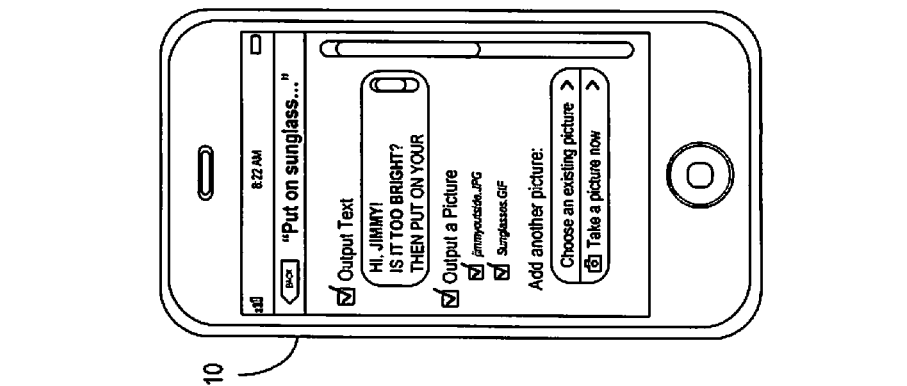

In the second example, illustrated by FIGS. 25A-C, a disabled user with sensitivity to light is prompted with both visual and audio assistive outputs upon detection of a brightness level that exceeds a threshold. For example, a caregiver may first specify a maximum level of brightness or brightness threshold (e.g., anything above "Normal Daylight" should trigger an assistive output), and then use a screen such as that of FIG. 25A to configure assistive outputs that should be produced upon the threshold being crossed (e.g., two pictures, some text, and an audio voice memo should be output). Turning to FIG. 25B, the disabled user may then carry the mobile terminal 10 into direct sunlight 74, such that a light sensor 76 detects that the predefined brightness threshold has been exceeded. (The screen of FIG. 25B announcing that the threshold has been succeeded may be optional.) The assistive outputs are then provided as shown in FIG. 25C, with text and pictures visually suggesting to the user to put on a pair of sunglasses (via display screen 16), along with an audio recommendation of the same (via integrated speaker 14, though alternately or additionally, a headset or headphones 58f may be employed).

Figure 26A:
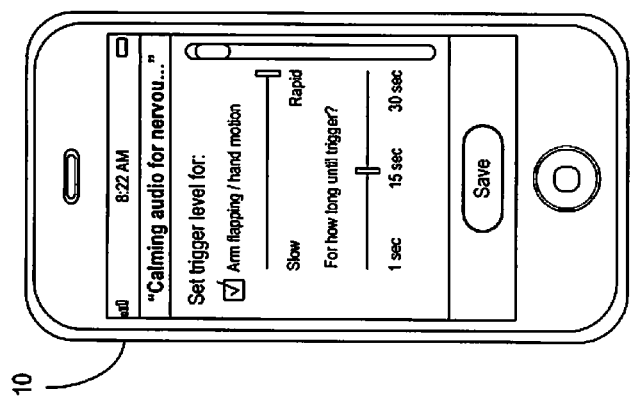
FIGS. 26A-C illustrate a twenty-fourth, twenty-fifth, and twenty-xisth screen shot associated with the flow chart of FIG. 5, as well as peripheral devices which may interface with a mobile terminal.
Figure 26B:
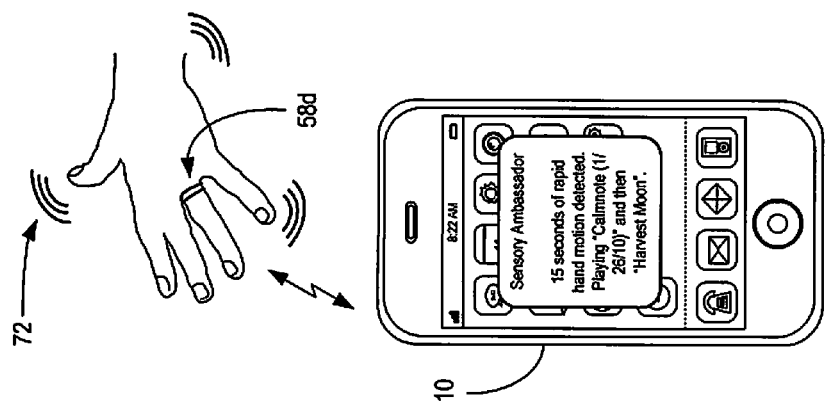
Figure 26C:
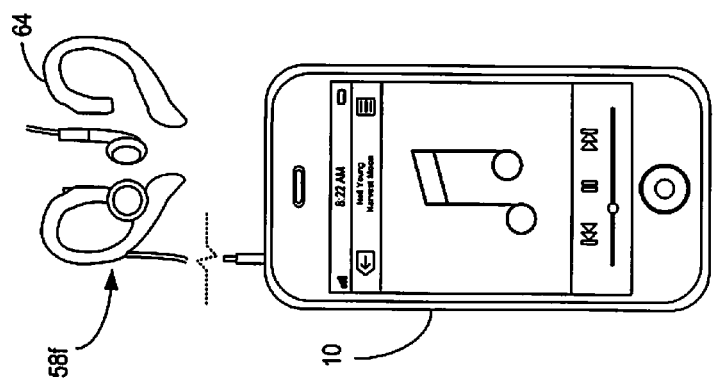

In the third example, illustrated by FIGS. 26A-C, a caregiver configures the software to output calming audio when it is detected that a disabled user (e.g., one with Down syndrome, Fragile X or autism) has been flapping his arms. In some cases, disabled individuals flap their arms or engage in other proprioceptive self-stimulatory behavior as a coping mechanism for sensory overstimulation. The caregiver in this example begins by setting trigger criteria as shown in FIG. 26A, whereby a level of hand motion (rapid) and length of motion activity (15 seconds) are specified. The mobile terminal 10 is then given to the disabled individual, who carries the device, and indeed begins to engage in self-stimulatory behavior, flapping his arms repeatedly for a period of time. As shown by FIG. 26B, using peripheral ring 58d, the motion activity is detected, though it should be understood that a variety of other sensors or technologies described herein may alternately or additionally be used in detecting such activity. FIG. 26B also depicts an example screen that may optionally be output at this time, including a text notification that at least 15 seconds of rapid hand motions have been detected, and so accordingly, two audio files will be output in sequence. The first, "Calmnote (1/26/10)", is a voice memo recorded by a caregiver in hopes of soothing or calming the individual when played (e.g., the caregiver says, "Jimmy: are you nervous or excited? Listen to your favorite song and take a deep breath"). The second, "Harvest Moon", is a song enjoyed particularly by the disabled individual during calmer moments. Turning to FIG. 26C, the mobile terminal 10 plays the audio through headphones 58f, though other output devices including speaker 14 and other types of peripheral headphones or headsets may be used.

Figure 27C:
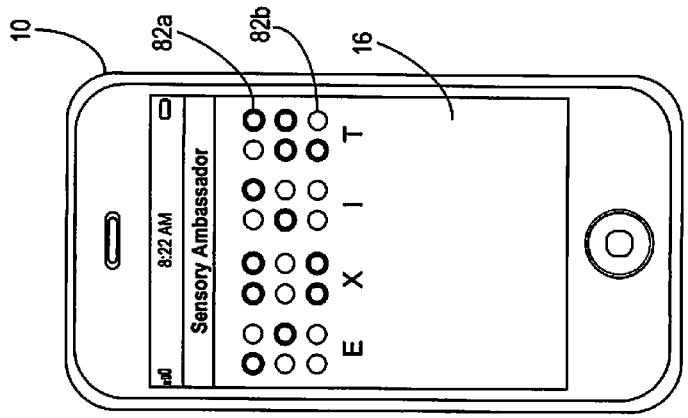
FIGS. 27A-C illustrate a twenty-seventh, twenty-eighth, and twenty-ninth screen shot associated with the flow chart of FIG. 5, as well as peripheral devices which may interface with a mobile terminal, and an environment surrounding the mobile terminal.
Figure 27B:
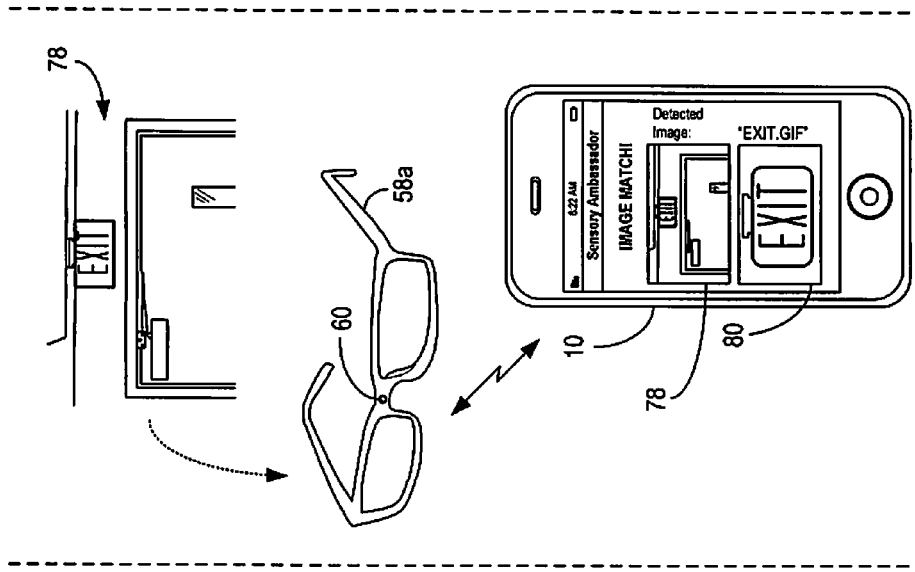
Figure 27A:
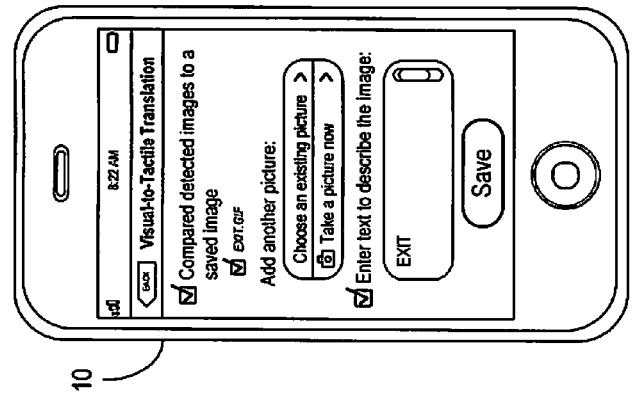

In the fourth example, illustrated by FIGS. 27A-C, a caregiver configures the software such that when a particular image is recognized by an optical camera communicatively coupled to the mobile terminal 10, a translatory tactile output is produced that describes the imaged. Such an arrangement may benefit a disabled user of the mobile terminal 10 who suffers from profound vision loss or blindness. As shown by FIG. 27A, a caregiver may begin by identifying an image, such as one stored within the memory of the mobile terminal that should be used as a benchmark to which a detected image may be compared. In this example, the caregiver has identified an image called "EXIT.GIF," which depicts a common EXIT sign. The caregiver also supplies text to describe the image (e.g., the caregiver uses a physical or virtual keyboard to type "EXIT"), and saves the configuration. Turning to FIG. 27B, the mobile terminal 10 is given to a disabled user, who also dons a pair of glasses 58a including an optical camera 60 (i.e., the glasses are worn as a fashionable, outward-facing camera, and are not necessarily used to enhance vision). Sure enough, a detected image 78 of an EXIT sign above a doorway matches a benchmark image 80 saved in memory of the device, causing a criterion to be satisfied and an assistive output to be produced. In this example, turning now to FIG. 27C, a tactile assistive output is produced, in the form of a pattern of raised portions of a touch screen 16. As shown, the pattern of raised portions of touch screen 16 represents the word "EXIT" in Braille. As described previously (with respect to U.S. Patent Application No. 2009/0174673 to Ciesla), cavities associated with portions of a touch screen may be inflated and deflated (with liquid or with air, administered by a pumping mechanism) to raise such portions in three dimensions. In this example, inflated cavities 82a are interspersed with deflated cavities 82b, creating four different Braille letters (each two-by-three matrix is associated with one letter). Thus, by running a finger across the touch screen 16, the disabled user may understand that an "EXIT" sign has been detected. Of course, alternate methods of representing words and pictures using tactile outputs may be employed as described above (e.g., those discussed with respect to the software developed by University of Tampere in Finland, which instead represents Braille characters using a series of vibrations of different intensities).

Of course, many other examples exist of sensory-translational, therapeutic and instructional outputs in response to a variety of events. In one example, an individual with poor thermoceptive capability carries a mobile terminal, and a thermometer detects a sudden and extreme increase in heat; audio speaker 14 then indicates "It's hot in here—please be careful" while a display screen 16 shows image of a thermometer, and a map of the environment indicating the location of "hot spots". In another example, a user suffers from a visual impairment, resulting in an inability to read. An optical camera detects a sign that says "Baseball Field Ahead". Headphones 58*f* may then output instructions routing the user to the baseball field (e.g., in conjunction with GPA technology). In another example, a caregiver specifies that a disabled user of a mobile terminal 10 is hypersensitive to certain types of sounds (e.g., sounds of crowds and heavy machinery). The mobile terminal 10 may then detect using GPS that it is approaching a geographic location known for such types of sounds (e.g., a shopping mall, a busy downtown area, a construction zone), and output an instruction to avoid the area. In another example, a sensor detects proximity to a nearby object on behalf of a user who is hyposensitive to visual-spatial sensation (depth perception), and alerts the individual to the presence of the object using audio. In another example, a user suffers impairments to the vestibular system, resulting in poor balance and motor planning. Over time, an accelerometer 34 and/or altimeter detect that the user seems to frequently lose his or her balance after eating. Accordingly, immediately after lunch every day, a "balance game" is output, focusing the user on balancing an object shown by the mobile terminal's display screen 16 (e.g., balance a bowling ball as it rolls down an alley), honing vestibular regulation. In another example, a user is hyposensitive to touch, and commonly engages in tactile-sensory-seeking behavior by banging or otherwise aggressively manipulating objects. A pressure sensor detects the user is clasping the mobile terminal 10 and/or pressing buttons with unnecessary force, and so the mobile terminal 10 vibrates vigorously such that user receives the tactile sensory stimulation he or she may have been seeking. In another example, a user may suffer from a proprioceptive deficit resulting in frequent fits of disorientation. An increased heart rate and increased level of electrodermal activity are detected. In response, an image of a caregiver is output via the display screen 16, along with a pre-recorded voice recording in which the caregiver says "It's OK, take a deep breath and sit down for a minute". In another example, a user has impairments related to both vision and equilibrioception. Whenever a high degree of motion is detected by a motion sensor, a warning is output for the user to proceed with caution.

The methods described above lend themselves to a database of saved user profiles. Such a database may store software settings in association with particular users (e.g., assistive output rules in accordance with "Jimmy Smith"). One exemplary user profile database is depicted by FIG. 28. As shown, each record of the user profile database may be given a unique identifier (e.g., P-0001). Each record may then store various data in association with the unique identifier. A profile name as entered by a caregiver may be saved (e.g., "Jimmy Smith"). An indication of whether or not the profile is currently loaded for use by the software may also be saved. Within each profile, various user-programmed settings may be stored. For example for each assistive output rule that is programmed, the database may store: (i) a first trigger (e.g., an indication of what should initiate an assistive output, such as a detected object near the mobile terminal 10); (ii) a first trigger type (e.g., lighting, physical movement, the presence of an object near a mobile terminal 10); (iii) any sensors or other technologies implicated in detecting the first trigger (e.g., a light sensor, a peripheral ring 56*d*, a motion sensor, an optical camera); (iv) a second trigger, second trigger type, and sensors implicated in detecting the second trigger (if applicable; not shown); (v) a date/time associated with the trigger, if applicable (e.g., the rule is "in effect" on Wednesday from 4:30 to 4:40 p.m.); (vi) one or more output types (e.g., visual, audio, tactile); and (vii) any content or instructions associated with an output (e.g., Rule 1 implicates the output of text "Hi Jimmy, Is it too bright? Then put on your sunglasses on" along with the output of two pictures, "jimmyoutside.JPG" and "Sunglasses.GIF"). Thus, as software of the present disclosure is programmed, data may be stored, and subsequently accessed to facilitate the execution of process steps shown by the flowchart of FIG. 5. If necessary, such a database may include other fields not shown by FIG. 28 (e.g., to indicate any preferences or other data associated with a rule, such as volume settings for an audio output, or a sequences in which images should be output). The database may be stored locally by mobile terminal 10, or by a central server in communication with the mobile terminal 10.

The methods described above may also lend themselves to a database of saved sensory deficiency and/or proficiency data associated with a user (i.e., a "sensory profile database"). Turning to FIG. 29, each record of the sensory profile database may be given a unique identifier (e.g., P-0001). Each record may then store various data in association with the unique identifier. A profile name as entered by a caregiver may be saved (e.g., "Jimmy Smith"). An indication of whether or not the profile is currently loaded for use by the software may also be saved. Within each profile, various data related to the sensory deficits and proficiencies of the user may be stored. For example, as users complete the processes of providing such data (whether by taking a survey, entering specific information related to a deficit, conducting a sensory evaluation, or importing data from another source), as described above with respect to blocks 104 and 106 of the flowchart of FIG. 5, the data may be stored in such a database. For demonstrative purposes, a limited number of fields for such data are illustrated by FIG. 29, though it should be understood that such a database may contain quite a bit more data in practice, and also may be organized differently. Nonetheless, the database of FIG. 29 stores: (i) answers to questions from a SPD survey (e.g., as shown in FIG. 10, the user "Always" expresses distress during grooming, "Frequently" limits self to certain textures/temperatures, and "Never" becomes anxious or distressed when feet leave the ground), (ii) an indication that the user has an impaired sense of smell, (iii) an indication that the user does not experience hyperacusis (oversensitivity to sounds), (iv) indications that the user suffers from moderate pulsatile tinnitus, (v) data indicating the user has "20/30" vision, (vi) indications that the user has severe tactile defensiveness to sand, and (vii) the results of a behavioral audiogram (e.g., demonstrating the lowest decibel level at which the user can hear certain frequencies of sounds in each ear).

In some embodiments, one or more fields of such a database may be updated based on the user's interaction with a mobile terminal. For example, initially, a user may hear sounds at 2000 Hz only when they occur at or above a level of 40 dB (e.g., database fields for "LEFT EAR @ 2000 Hz" and "RIGHT EAR @ 2000 Hz may both store an indication of "40 dB," based on a first sensory evaluation conducted when the user began using the software). However, over time, the user's level of hearing may decline. Such a decline may be detected (i) in response to normal use of the mobile terminal (e.g., as sounds are periodically output at a frequency of 2000 Hz, the software determines that the user is less and less responsive to them), and/or (ii) as a result of a second sensory evaluation (e.g., one month after the user performs a first hearing test, a second hearing test is conducted, producing a new behavioral audiogram, such that the sensory profile database may be updated with new information on the user's hearing). For example, if the user's ability to hear sounds emitted at a frequency of 2000 Hz has decreased to the point where only sounds above a level of 50 dB are heard, the sensory profile database may be so updated. Of course, other sensory deficit and proficiency information besides hearing information may be so updated (e.g., a user is originally thought to be severely tactile defensive, but over time does not demonstrate dissatisfaction in response to the mobile terminal's vibrations (the user does not drop the device or express an emotional outburst), and so the user's tactile defensiveness may be downgraded from severe).

In other embodiments, one or more fields of a sensory profile database based on data specifically entered by a user related to a deficit. For example, a user may take a new survey, or otherwise enter or import new information.

In any case, as the data in the sensory profile database of FIG. 29 evolve over time, so may the assistive rules stored within the user profile database of FIG. 28. For example, as described above, the software may contain logic for automatically creating (or editing existing) rules based on patterns or correlations of sensory profile data. For example, logic of the software may dictate that if a user's level of hearing drops from 40 dB to 50 dB at 2000 Hz, not only should an image be output, but a tactile vibration should also be produced (e.g., a field for "OUTPUT CONTENT 2" within the database of FIG. 28 is automatically changed from "N/A" to "MED. VIBRATE; UNTIL PICKED UP"). Thus, in some embodiments, the database of FIG. 28 may automatically react to changes within the database of FIG. 29.

While the above discussion provides a particularly contemplated set of embodiments, the present disclosure is not so limited. Numerous alternate embodiments are also possible and within the scope of the present disclosure. These alternate embodiments are not necessarily mutually exclusive with one another or with the embodiments set forth above. Rather, components of the various embodiments may be mixed and matched as needed or desired. In one alternate embodiment, when a user configures an assistive output (e.g., as shown by the screen of FIG. 23), the user may select an option to import a preexisting visual or audiovisual aid created using a separate software program. For example, the IPROMPTS® application as developed by HANDHOLD ADAPTIVE® of Shelton, Conn., allows users of the APPLE™ IPHONE™ and IPOD™ TOUCH to create and present visual picture schedules, visual countdown timers, and visual choice boards to those with language and behavioral challenges (many of whom also suffer from sensory challenges). Such a preexisting schedule incorporating pictures and text may be imported within the software of the present disclosure, and used as an assistive output. Methods for the creation and presentation of such visual aids are described in Applicants' co-pending U.S. patent application Ser. No. 12/391,871, filed Feb. 24, 2009 and entitled "Portable Prompting Aid for the Developmentally Disabled"; the entirety of this document is incorporated by reference for all purposes.

In some embodiments, a log of assistive output activity may be maintained. For example, each time an assistive output is triggered, an indication of the output may be stored in a database (not shown). The database may store: (i) a time/date when the assistive output was generated, (ii) the trigger for the assistive output, (iii) the type of assistive output, and (iv) information related to events that transpired before or the assistive output was produced (e.g., the database stores an electronic audio or video file of the user reacting to the output, an indication of any buttons pressed on the mobile terminal 10 after the output was produced, the current temperature or level of lighting at the time of the output, etc.). Thus, those not present at the time of the assistive output (e.g., caregivers) may review the context in which a particular assistive outputs is produced, or may review the data for trends (e.g., certain types of assistive outputs are less common during the past month, perhaps indicating one of the user's sensory deficits is improving). For example, a child's log indicates he more frequently covers his ears when the source of the noise is not man-made (e.g., tractors, busses, televisions), and seems to struggle with his balance more in the morning than at night. In another example, a user is more commonly bothered by bright environments when the environment is also noisy, or it is winter time. Such data may be accessible through the user's mobile terminal 10, may be uploaded or transmit to another mobile terminal 10 or computer 54. For example, the message shown by the screen of FIG. 26B is passed to a caregiver's mobile terminal 10 as an alternative or in addition to appearing on a disabled user's mobile terminal 10.

In some embodiments, a remote observant may monitor the environment of a disabled individual. For example, a video or still camera transmits images from the disabled individual's mobile terminal 10 to a separate computing device (e.g., another mobile terminal or a personal computer), such that a remote observant (e.g., caregiver, therapist, call center employee) can view the images being sent in substantially real time. For example, an audio feed is transmitted to a remote parent, who can "listen in" to her child's environment. In another example, data from various sensors of the mobile terminal 10 may be uploaded to a central monitoring Web site allowing those with access to view current environmental data associated with a disabled individual.

Rules of Interpretation & General Definitions

Numerous embodiments are described in this disclosure, and are presented for illustrative purposes only. The described embodiments are not, and are not intended to be, limiting in any sense. The presently disclosed invention(s) are widely applicable to numerous embodiments, as is readily apparent from the disclosure. One of ordinary skill in the art will recognize that the disclosed invention(s) may be practiced with various modifications and alterations, such as structural, logical, software, and electrical modifications. Although particular features of the disclosed invention(s) may be described with reference to one or more particular embodiments and/or drawings, it should be understood that such features are not limited to usage in the one or more particular embodiments or drawings with reference to which they are described, unless expressly specified otherwise.

The present disclosure is neither a literal description of all embodiments nor a listing of features of the invention that must be present in all embodiments.

Neither the Title (set forth at the beginning of the first page of this disclosure) nor the Abstract (set forth at the end of this disclosure) is to be taken as limiting in any way as the scope of the disclosed invention(s).

The term "product" means any machine, manufacture and/or composition of matter as contemplated by 35 U.S.C. §101, unless expressly specified otherwise.

The terms "an embodiment", "embodiment", "embodiments", "the embodiment", "the embodiments", "one or more embodiments", "some embodiments", "one embodiment" and the like mean "one or more (but not all) disclosed embodiments", unless expressly specified otherwise.

The terms "the invention" and "the present invention" and the like mean "one or more embodiments of the present invention."

A reference to "another embodiment" in describing an embodiment does not imply that the referenced embodiment is mutually exclusive with another embodiment (e.g., an embodiment described before the referenced embodiment), unless expressly specified otherwise.

The terms "including", "comprising" and variations thereof mean "including but not limited to", unless expressly specified otherwise.

The terms "a", "an" and "the" mean "one or more", unless expressly specified otherwise.

The term "plurality" means "two or more", unless expressly specified otherwise.

The term "herein" means "in the present disclosure, including anything which may be incorporated by reference", unless expressly specified otherwise.

The phrase "at least one of", when such phrase modifies a plurality of things (such as an enumerated list of things) means any combination of one or more of those things, unless expressly specified otherwise. For example, the phrase at least one of a widget, a car and a wheel means either (i) a widget, (ii) a car, (iii) a wheel, (iv) a widget and a car, (v) a widget and a wheel, (vi) a car and a wheel, or (vii) a widget, a car and a wheel.

The phrase "based on" does not mean "based only on", unless expressly specified otherwise. In other words, the phrase "based on" describes both "based only on" and "based at least on".

Where a limitation of a first claim would cover one of a feature as well as more than one of a feature (e.g., a limitation such as "at least one widget" covers one widget as well as more than one widget), and where in a second claim that depends on the first claim, the second claim uses a definite article "the" to refer to the limitation (e.g., "the widget"), this does not imply that the first claim covers only one of the feature, and this does not imply that the second claim covers only one of the feature (e.g., "the widget" can cover both one widget and more than one widget).

Each process (whether called a method, algorithm or otherwise) inherently includes one or more steps, and therefore all references to a "step" or "steps" of a process have an inherent antecedent basis in the mere recitation of the term 'process' or a like term. Accordingly, any reference in a claim to a 'step' or 'steps' of a process has sufficient antecedent basis.

When an ordinal number (such as "first", "second", "third" and so on) is used as an adjective before a term, that ordinal number is used (unless expressly specified otherwise) merely to indicate a particular feature, such as to distinguish that particular feature from another feature that is described by the same term or by a similar term. For example, a "first widget" may be so named merely to distinguish it from, e.g., a "second widget". Thus, the mere usage of the ordinal numbers "first" and "second" before the term "widget" does not indicate any other relationship between the two widgets, and likewise does not indicate any other characteristics of either or both widgets. For example, the mere usage of the ordinal numbers "first" and "second" before the term "widget" (1) does not indicate that either widget comes before or after any other in order or location; (2) does not indicate that either widget occurs or acts before or after any other in time; and (3) does not indicate that either widget ranks above or below any other, as in importance or quality. In addition, the mere usage of ordinal numbers does not define a numerical limit to the features identified with the ordinal numbers. For example, the mere usage of the ordinal numbers "first" and "second" before the term "widget" does not indicate that there must be no more than two widgets.

When a single device or article is described herein, more than one device or article (whether or not they cooperate) may alternatively be used in place of the single device or article that is described. Accordingly, the functionality that is described as being possessed by a device may alternatively be possessed by more than one device or article (whether or not they cooperate).

Similarly, where more than one device or article is described herein (whether or not they cooperate), a single device or article may alternatively be used in place of the more than one device or article that is described. For example, a plurality of computer-based devices may be substituted with a single computer-based device. Accordingly, the various functionality that is described as being possessed by more than one device or article may alternatively be possessed by a single device or article.

The functionality and/or the features of a single device that is described may be alternatively embodied by one or more other devices that are described but are not explicitly described as having such functionality and/or features. Thus, other embodiments need not include the described device itself, but rather can include the one or more other devices which would, in those other embodiments, have such functionality/features.

Devices that are in communication with each other need not be in continuous communication with each other, unless expressly specified otherwise. On the contrary, such devices need only transmit to each other as necessary or desirable, and may actually refrain from exchanging data most of the time. For example, a machine in communication with another machine via the Internet may not transmit data to the other machine for weeks at a time. In addition, devices that are in communication with each other may communicate directly or indirectly through one or more intermediaries.

A description of an embodiment with several components or features does not imply that all or even any of such components and/or features are required. On the contrary, a variety of optional components are described to illustrate the wide variety of possible embodiments of the present disclosure. Unless otherwise specified explicitly, no component and/or feature is essential or required.

Further, although process steps, algorithms or the like may be described in a sequential order, such processes may be configured to work in different orders. In other words, any sequence or order of steps that may be explicitly described does not necessarily indicate a requirement that the steps be performed in that order. The steps of processes described herein may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to the invention, and does not imply that the illustrated process is preferred.

Although a process may be described as including a plurality of steps, that does not indicate that all or even any of the steps are essential or required. Various other embodiments within the scope of the described invention(s) include other processes that omit some or all of the described steps. Unless otherwise specified explicitly, no step is essential or required.

Although a product may be described as including a plurality of components, aspects, qualities, characteristics and/or features, that does not indicate that all of the plurality are essential or required. Various other embodiments within the scope of the described invention(s) include other products that omit some or all of the described plurality.

An enumerated list of items (which may or may not be numbered) does not imply that any or all of the items are mutually exclusive, unless expressly specified otherwise. Likewise, an enumerated list of items (which may or may not be numbered) does not imply that any or all of the items are comprehensive of any category, unless expressly specified otherwise. For example, the enumerated list "a computer, a laptop, a PDA" does not imply that any or all of the three items of that list are mutually exclusive and does not imply that any or all of the three items of that list are comprehensive of any category.

Headings of sections provided in this disclosure are for convenience only, and are not to be taken as limiting the disclosure in any way.

"Determining" something can be performed in a variety of manners and therefore the term "determining" (and like terms) includes calculating, computing, deriving, looking up (e.g., in a table, database or data structure), ascertaining, recognizing, and the like.

A "display" as that term is used herein is an area that conveys information to a viewer. The information may be dynamic, in which case, an LCD, LED, CRT, LDP, rear projection, front projection, or the like may be used to form the display. The aspect ratio of the display may be 4:3, 16:9, or the like. Furthermore, the resolution of the display may be any appropriate resolution such as 480i, 480p, 720p, 1080i, 1080p or the like. The format of information sent to the display may be any appropriate format such as standard definition (SDTV), enhanced definition (EDTV), high definition (HD), or the like. The information may likewise be static, in which case, painted glass may be used to form the display. Note that static information may be presented on a display capable of displaying dynamic information if desired.

The present disclosure frequently refers to a "control system". A control system, as that term is used herein, may be a computer processor coupled with an operating system, device drivers, and appropriate programs (collectively "software") with instructions to provide the functionality described for the control system. The software is stored in an associated memory device (sometimes referred to as a computer readable medium). While it is contemplated that an appropriately programmed general purpose computer or computing device may be used, it is also contemplated that hard-wired circuitry or custom hardware (e.g., an application specific integrated circuit (ASIC)) may be used in place of, or in combination with, software instructions for implementation of the processes of various embodiments. Thus, embodiments are not limited to any specific combination of hardware and software.

A "processor" means any one or more microprocessors, CPU devices, computing devices, microcontrollers, digital signal processors, or like devices. Exemplary processors are the INTEL PENTIUM or AMD ATHLON processors.

The term "computer-readable medium" refers to any medium that participates in providing data (e.g., instructions) that may be read by a computer, a processor or a like device. Such a medium may take many forms, including but not limited to, non-volatile media, volatile media, and transmission media. Non-volatile media include, for example, optical or magnetic disks and other persistent memory. Volatile media include DRAM, which typically constitutes the main memory. Transmission media include coaxial cables, copper wire and fiber optics, including the wires that comprise a system bus coupled to the processor. Transmission media may include or convey acoustic waves, light waves and electromagnetic emissions, such as those generated during RF and IR data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, a USB memory stick, a dongle, any other memory chip or cartridge, a carrier wave, or any other medium from which a computer can read.

Various forms of computer readable media may be involved in carrying sequences of instructions to a processor. For example, sequences of instruction (i) may be delivered from RAM to a processor, (ii) may be carried over a wireless transmission medium, and/or (iii) may be formatted according to numerous formats, standards or protocols. For a more exhaustive list of protocols, the term "network" is defined below and includes many exemplary protocols that are also applicable here.

It will be readily apparent that the various methods and algorithms described herein may be implemented by a control system and/or the instructions of the software may be designed to carry out the processes of the present disclosure.

Where databases are described, it will be understood by one of ordinary skill in the art that (i) alternative database structures to those described may be readily employed, and (ii) other memory structures besides databases may be readily employed. Any illustrations or descriptions of any sample databases presented herein are illustrative arrangements for stored representations of information. Any number of other arrangements may be employed besides those suggested by, e.g., tables illustrated in drawings or elsewhere. Similarly, any illustrated entries of the databases represent exemplary information only; one of ordinary skill in the art will understand that the number and content of the entries can be different from those described herein. Further, despite any depiction of the databases as tables, other formats (including relational databases, object-based models, hierarchical electronic file structures, and/or distributed databases) could be used to store and manipulate the data types described herein. Likewise, object methods or behaviors of a database can be used to implement various processes, such as those described herein. In addition, the databases may, in a known manner, be stored locally or remotely from a device that accesses data in such a database. Furthermore, while unified databases may be contemplated, it is also possible that the databases may be distributed and/or duplicated amongst a variety of devices.

As used herein a "network" is an environment wherein one or more computing devices may communicate with one another. Such devices may communicate directly or indirectly, via a wired or wireless medium such as the Internet, Local Area Network (LAN), Wide Area Network (WAN), or Ethernet (or IEEE 802.3), Token Ring, or via any appropriate communications means or combination of communications means. Exemplary protocols include but are not limited to: BLUETOOTH™, TDMA, CDMA, GSM, EDGE, GPRS, WCDMA, AMPS, D-AMPS, IEEE 802.11 (WI-FI), IEEE 802.3, TCP/IP, or the like. Note that if video signals or large files are being sent over the network, a broadband network may be used to alleviate delays associated with the transfer of such large files, however, such is not strictly required. Each of the devices is adapted to communicate on such a communication means. Any number and type of machines may be in communication via the network. Where the network is the Internet, communications over the Internet may be through a website maintained by a computer on a remote server or over an online data network including commercial online service providers, bulletin board systems, and the like. In yet other embodiments, the devices may communicate with one another over RF, cellular networks, cable TV, satellite links, and the like. Where appropriate encryption or other security measures such as logins and passwords may be provided to protect proprietary or confidential information.

Communication among computers and devices may be encrypted to insure privacy and prevent fraud in any of a variety of ways well known in the art. Appropriate cryptographic protocols for bolstering system security are described in Schneier, APPLIED CRYPTOGRAPHY, PROTOCOLS, ALGORITHMS, AND SOURCE CODE IN C, John Wiley & Sons, Inc. 2d ed., 1996, which is incorporated by reference in its entirety.

The present disclosure provides, to one of ordinary skill in the art, an enabling description of several embodiments and/or inventions. Some of these embodiments and/or inventions may not be claimed in the present disclosure, but may nevertheless be claimed in one or more continuing applications that claim the benefit of priority of the present disclosure.

What is claimed is:

1. A mobile terminal comprising:
    a plurality of sensors, wherein the plurality of sensors includes at least two sensors from a group that includes sensors operable to detect light, sound, motion, temperature, geographic location, blood glucose level, blood pressure, electrodermal skin response, or heart rate;
    a user interface, wherein the user interface includes at least one of a touch-sensitive display screen, an audio speaker, and a vibration unit as a user interface component; and
    a control system operatively coupled to the plurality of sensors and the user interface and adapted to:
    receive profile information associated with a user of the mobile terminal, wherein the profile information is stored electronically in a database and defines:
    a sensory disability associated with the user of the mobile terminal, wherein the sensory disability comprises at least one among a vision, hearing, locomotion, balance, smell, and touch disability;
    a sensory proficiency associated with the user of the mobile terminal, wherein the sensory proficiency comprises a vision, hearing, or touch proficiency;
    an assistive output rule, which associates the sensory disability with at least one sensor from the plurality of sensors, associates the sensory proficiency with at least one user interface component, and associates the sensory disability with the sensory proficiency, such that at least one user interface component is employed in a manner that compensates for the sensory disability; and
    an event comprising a threshold criterion associated with the at least one sensor from the plurality of sensors;
    compare a measurement from the at least one sensor to the threshold criterion to determine if the event has occurred; and
    execute the assistive output rule by employing the at least one user interface component so as to compensate for the sensory deficit of the user such that the user perceives the event through a sense associated with the sensory proficiency and does not have to rely on a sense associated with the sensory disability to perceive the event.

2. The mobile terminal of claim 1 wherein the at least one sensor comprises a sensor positioned within a housing of the mobile terminal.

3. The mobile terminal of claim 1 wherein the at least one sensor comprises a peripheral device positioned outside of a housing of the mobile terminal.

4. The mobile terminal of claim 3 wherein the peripheral device is selected from the group consisting of: eyeglasses, skin patch, watch, ring, microphone, headphones, and camera.

5. The mobile terminal of claim 4 wherein the peripheral device comprises a plurality of elements within the group within a single housing.

6. The mobile terminal of claim 1 wherein the control system is adapted to receive the profile from a caregiver.

7. The mobile terminal of claim 1 wherein the control system is further adapted to use a sensor to determine if the mobile terminal is positioned in a desired configuration and output a reminder to position the mobile terminal in the desired configuration.

8. The mobile terminal of claim 1 wherein the control system is further adapted to receive the profile information by evaluating survey responses.

9. The mobile terminal of claim 1 wherein the control system is further adapted to receive the profile information by evaluating selections made from a prepopulated list.

10. The mobile terminal of claim 1 wherein the control system is further adapted to receive the profile information by evaluating results from a diagnosis received through direct testing.

11. The mobile terminal of claim 1 wherein the assistive output uses a combination of user interface components.

12. The mobile terminal of claim 1 wherein the sensory disability comprises a hearing deficit and the sensory proficiency comprises a touch proficiency.

13. The mobile terminal of claim 12 wherein the hearing deficit comprises hypersensitivity or hyposensitivity to sound.

14. The mobile terminal of claim 1 wherein the sensory disability comprises a vision deficit and the sensory proficiency comprises a hearing proficiency.

15. The mobile terminal of claim 14 wherein the vision deficit comprises hypersensitivity or hyposensitivity to light.

16. The mobile terminal of claim 1 wherein the sensory disability comprises a balance deficit and the sensory proficiency comprises a vision proficiency.

17. The mobile terminal of claim 1 wherein the sensory disability comprises a touch deficit and the sensory proficiency comprises a hearing proficiency.

* * * * *